United States Patent [19]
Yoon

[11] Patent Number: 5,984,932
[45] Date of Patent: *Nov. 16, 1999

[54] SUTURING INSTRUMENT WITH ONE OR MORE SPREADABLE NEEDLE HOLDERS MOUNTED FOR ARCUATE MOVEMENT

[76] Inventor: InBae Yoon, 2101 Highland Ridge Dr., Phoenix, Md. 21131

[*] Notice: This patent issued on a continued prosecution application filed under 37 CFR 1.53(d), and is subject to the twenty year patent term provisions of 35 U.S.C. 154(a)(2).

[21] Appl. No.: 08/847,182

[22] Filed: May 1, 1997

Related U.S. Application Data

[63] Continuation-in-part of application No. 08/758,648, Nov. 27, 1996.

[51] Int. Cl.⁶ .................................................. A61B 17/04
[52] U.S. Cl. ........................................... 606/147; 606/148
[58] Field of Search ............................. 606/139, 144–148

[56] References Cited

U.S. PATENT DOCUMENTS

| | | | |
|---|---|---|---|
| 919,138 | 4/1909 | Drake et al. . | |
| 1,037,864 | 9/1912 | Carlson et al. . | |
| 1,449,087 | 3/1923 | Bugbee . | |
| 1,822,330 | 9/1931 | Ainslie | 606/148 |
| 2,213,830 | 9/1940 | Anastasi . | |
| 2,646,045 | 7/1953 | Priestley . | |
| 2,959,172 | 11/1960 | Held . | |
| 3,090,386 | 5/1963 | Curtis . | |
| 3,139,089 | 6/1964 | Schwerin . | |
| 3,349,772 | 10/1967 | Rygg | 606/147 |
| 3,470,875 | 10/1969 | Johnson . | |
| 3,842,840 | 10/1974 | Schweizer | 606/148 |
| 3,946,740 | 3/1976 | Bassett . | |
| 4,109,658 | 8/1978 | Hughes . | |
| 4,164,225 | 8/1979 | Johnson et al. | 606/144 |
| 4,440,171 | 4/1984 | Nomoto et al. | 606/144 |
| 4,557,265 | 12/1985 | Andersson . | |
| 4,621,640 | 11/1986 | Mulhollan et al. | 606/144 |
| 4,635,638 | 1/1987 | Weintraub et al. | 606/147 |
| 4,935,027 | 6/1990 | Yoon | 606/147 |
| 5,037,433 | 8/1991 | Wilk et al. | 606/139 |
| 5,100,421 | 3/1992 | Christoudias | 606/147 |
| 5,147,373 | 9/1992 | Ferzli | 606/144 |
| 5,181,919 | 1/1993 | Bergman et al. . | |

(List continued on next page.)

FOREIGN PATENT DOCUMENTS

WO 97/37583   10/1997   WIPO .

*Primary Examiner*—Gary Jackson
*Attorney, Agent, or Firm*—Blank Rome Comisky & McCauley LLP

[57] ABSTRACT

An instrument for suturing anatomical tissue with a suture needle includes a housing, an elongate tubular member mounted by the housing, a needle driver having a distal end movable between an undeployed position disposed laterally inward of a peripheral edge of the elongate tubular member and a deployed position disposed laterally outward of the peripheral edge, and a needle catcher having a distal end movable between an undeployed position disposed laterally inward of the peripheral edge of the elongate tubular member and a deployed position disposed laterally outward of the peripheral edge. At least one of the needle driver and the needle catcher is coupled with the housing for arcuate movement about a longitudinal axis of the elongate tubular member such that a corresponding distal end of the needle holder is caused to move along an arcuate path having a radius of curvature greater than a radial dimension of the elongate tubular member. In addition, the respective distal ends of the needle driver and the needle catcher are operable to grasp and release the suture needle so that, when the needle driver and the needle catcher are in deployed positions, a suture needle having a radius of curvature commensurate with the radius of curvature of the arcuate path can be driven through anatomical tissue using a distal end of the needle driver and can be subsequently passed to the distal end of the needle catcher to be pulled through the anatomical tissue.

34 Claims, 9 Drawing Sheets

U.S. PATENT DOCUMENTS

| | | | |
|---|---|---|---|
| 5,211,650 | 5/1993 | Noda . | |
| 5,222,508 | 6/1993 | Contarini . | |
| 5,234,443 | 8/1993 | Phan et al. | 606/148 |
| 5,244,948 | 9/1993 | Mulhaupt et al. . | |
| 5,261,917 | 11/1993 | Hasson et al. | 606/148 |
| 5,281,238 | 1/1994 | Chin et al. . | |
| 5,304,185 | 4/1994 | Taylor . | |
| 5,308,353 | 5/1994 | Beurrier . | |
| 5,320,632 | 6/1994 | Heidmueller . | |
| 5,336,230 | 8/1994 | Leichtling et al. | 606/148 |
| 5,336,231 | 8/1994 | Adair | 606/148 |
| 5,356,424 | 10/1994 | Buzerak et al. . | |
| 5,364,408 | 11/1994 | Gordon . | |
| 5,364,409 | 11/1994 | Kuwabara et al. . | |
| 5,374,275 | 12/1994 | Bradley et al. . | |
| 5,376,096 | 12/1994 | Foster . | |
| 5,389,098 | 2/1995 | Tsuruta et al. . | |
| 5,389,103 | 2/1995 | Melzer et al. . | |
| 5,395,367 | 3/1995 | Wilk . | |
| 5,397,325 | 3/1995 | Della Badia et al. . | |
| 5,403,328 | 4/1995 | Shallman . | |
| 5,403,329 | 4/1995 | Hinchcliffe . | |
| 5,437,681 | 8/1995 | Meade et al. . | |
| 5,454,823 | 10/1995 | Richardson et al. . | |
| 5,462,561 | 10/1995 | Voda . | |
| 5,462,562 | 10/1995 | Elkus . | |
| 5,468,251 | 11/1995 | Buelna . | |
| 5,470,338 | 11/1995 | Whitfield et al. . | |
| 5,474,057 | 12/1995 | Makower et al. . | |
| 5,474,568 | 12/1995 | Scott . | |
| 5,477,794 | 12/1995 | Klundt . | |
| 5,478,344 | 12/1995 | Stone et al. . | |
| 5,478,345 | 12/1995 | Stone et al. . | |
| 5,480,406 | 1/1996 | Nolan et al. . | |
| 5,496,334 | 3/1996 | Klundt et al. . | |
| 5,503,634 | 4/1996 | Christy . | |
| 5,520,703 | 5/1996 | Essig et al. . | |
| 5,540,704 | 7/1996 | Gordon et al. | 606/144 |
| 5,540,705 | 7/1996 | Meade et al. | 606/145 |
| 5,545,148 | 8/1996 | Wurster . | |
| 5,562,640 | 10/1996 | McCabe et al. . | |
| 5,562,685 | 10/1996 | Mollenauer et al. . | |
| 5,562,686 | 10/1996 | Sauer et al. | 606/144 |
| 5,562,703 | 10/1996 | Desai . | |
| 5,569,164 | 10/1996 | Lurz . | |
| 5,569,269 | 10/1996 | Hart et al. . | |
| 5,569,270 | 10/1996 | Weng . | |
| 5,573,542 | 11/1996 | Stevens . | |
| 5,578,048 | 11/1996 | Pasqualucci et al. . | |
| 5,582,617 | 12/1996 | Klieman et al. | 606/170 |
| 5,591,181 | 1/1997 | Stone et al. | 606/144 |
| 5,601,575 | 2/1997 | Measamer et al. . | |
| 5,607,435 | 3/1997 | Sachdeva et al. . | |
| 5,609,601 | 3/1997 | Kolesa et al. | 606/110 |
| 5,626,588 | 5/1997 | Sauer et al. . | |
| 5,632,751 | 5/1997 | Piraka . | |
| 5,632,752 | 5/1997 | Buelna . | |
| 5,643,292 | 7/1997 | Hart . | |
| 5,662,663 | 9/1997 | Shallman . | |
| 5,674,230 | 10/1997 | Tovey et al. . | |
| 5,707,379 | 1/1998 | Fleenor et al. . | |
| 5,709,693 | 1/1998 | Taylor . | |
| 5,709,694 | 1/1998 | Greenberg et al. . | |

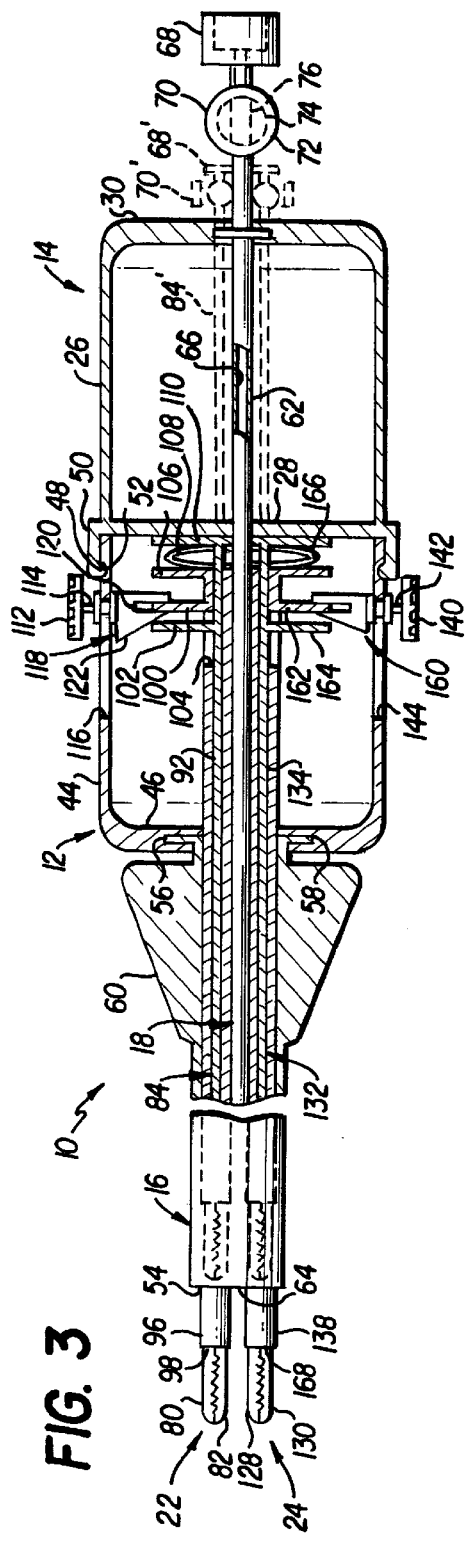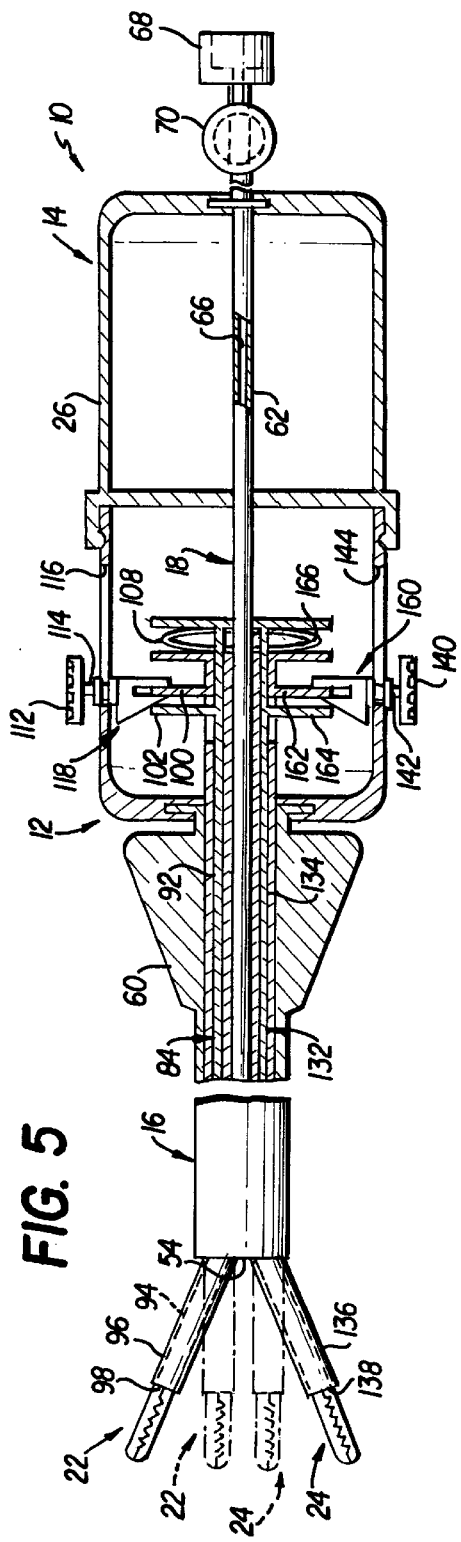
FIG. 3
FIG. 5

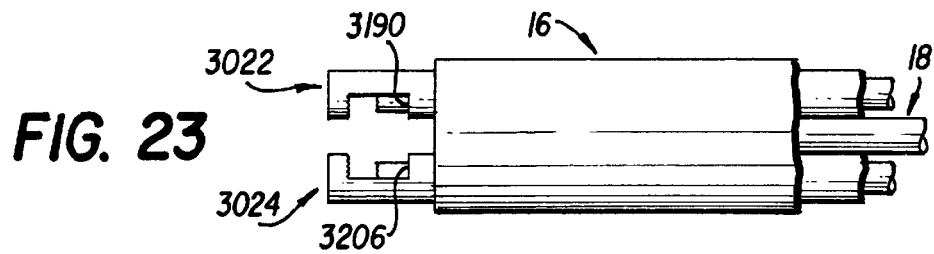
FIG. 23
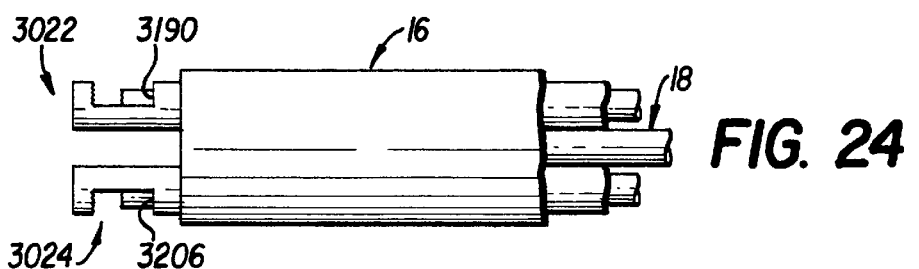
FIG. 24
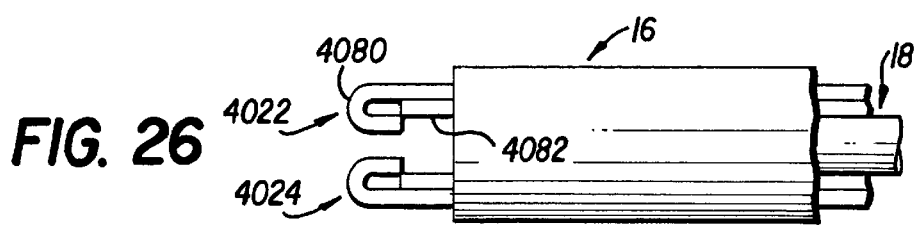
FIG. 26
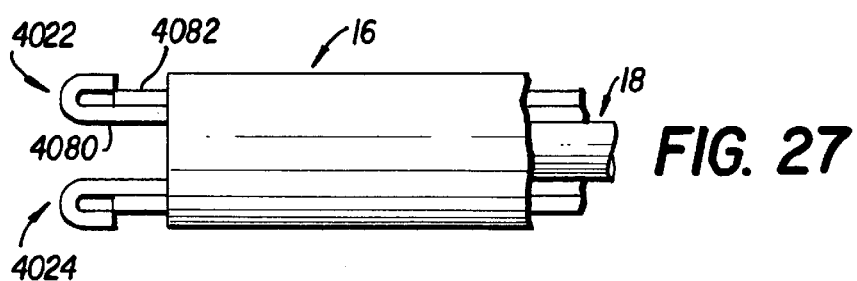
FIG. 27
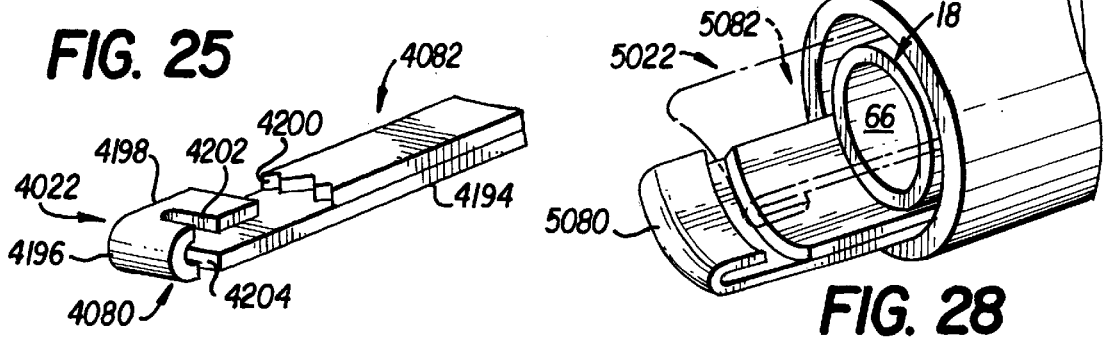
FIG. 25
FIG. 28

SUTURING INSTRUMENT WITH ONE OR MORE SPREADABLE NEEDLE HOLDERS MOUNTED FOR ARCUATE MOVEMENT

CROSS-REFERENCE TO RELATED APPLICATIONS

This application is a continuation-in-part of application Ser. No. 08/758,648, filed Nov. 27, 1996, the disclosure of which is incorporated herein by reference.

BACKGROUND OF THE INVENTION

1. Field of the Invention

The present invention pertains to suturing of bodily or anatomical tissue and, more particularly, to an apparatus and method for suturing anatomical tissue during endoscopic and open surgical procedures.

2. Discussion of the Related Art

Suturing of bodily tissue, that is, the practice of using lengths of suture material to ligate or approximate tissue, is a time consuming part of most surgical procedures including both open surgery and endoscopic or closed surgery. By "open surgery" is meant surgery wherein the surgeon gains access to the surgical site by a relatively large incision and by "endoscopic surgery" is meant minimally invasive surgery wherein the surgeon gains access to the surgical site via one or more portals through which endoscopes are introduced to view the surgical site and through which instruments, such as forceps, cutters, needle holders and the like, are introduced to the surgical site.

In the past, suturing has been accomplished with the use of a sharp suture needle carrying a length of suture material, the suture needle being caused to penetrate and pass through the tissue pulling the suture material through the tissue. Once the suture material has been pulled through the tissue, the surgeon ties a knot in the suture material, the knotting procedure allowing the surgeon to adjust the tension on the suture material to accommodate the particular tissue being sutured and to control approximation, occlusion, attachment or other conditions of the tissue.

The process of tissue penetration and knotting of the suture material can be time consuming and tedious work, particularly when performed in connection with microsurgery and endoscopic surgery and can unduly prolong the duration of surgery and therefore the period in which the patient is under anesthesia. Nevertheless, endoscopic surgery is preferred over open surgery due to the greatly reduced trauma and wound healing time for the patient and due to cost savings associated with shorter hospital stays and performing surgery in non-hospital or out-patient surgery sites. Accordingly, there has been much effort to develop techniques for facilitating the suturing normally performed by use of a suture needle and a length of suture material. Alternative techniques proposed have included electrical coagulation, mechanical devices such as clips, clamps and staples, and lasers; however, no alternative technique has yet been well accepted by surgeons to produce the results obtained by suturing and tying. Thus, there is a great need for suturing techniques useful in open and endoscopic surgery to permit surgeons to suture anatomical tissue using suture needles and lengths of suture material in a time efficient, consistent and precise manner.

The performance of an endoscopic procedure typically involves creation of one or a number of puncture sites through a wall of an anatomical cavity using a penetrating instrument including an obturator, such as a trocar, disposed within a portal sleeve. After the penetrating instrument has penetrated into the anatomical cavity, the obturator is withdrawn leaving the sleeve in place to form a portal in the cavity wall for the introduction of instruments such as endoscopes, scissors, forceps, needle holders and the like into the anatomical cavity. Suturing is typically performed with a needle holding instrument or holder having a pair of jaws adapted to hold the body of a suture needle. The jaws of the needle holding instrument are inserted through the portal sleeve and are positioned at the operative site by manipulation of a handle at the proximal end of the instrument outside the body. With a suture needle held between the jaws of the needle holding instrument, the handle is manipulated to cause a tip of the needle to be pushed through the tissue being sutured. Once the tip of the suture needle has been pushed through the tissue, the jaws of the needle holding instrument must either be opened to release the suture needle so that the tip of the needle can be grasped and pulled through the tissue therewith, or a second needle holding instrument must be introduced at the operative site through another portal to grasp the tip of the suture needle after it has emerged from the tissue being sutured. The former technique requires further adjustment of the suture needle within the jaws of the needle holder before another stitch can be made; and, while use of a second needle holding instrument for pulling the needle through the anatomical tissue allows the first needle holding instrument to grasp the body of the suture needle in the manner required to make additional stitches, it is generally desirable to minimize the number of puncture sites created for performing a particular endoscopic procedure.

SUMMARY OF THE INVENTION

Accordingly, it is a primary object of the present invention to overcome the above-mentioned disadvantages of the prior art and to improve suturing instruments and methods of suturing anatomical tissue.

Another object of the present invention is to permit suturing of anatomical tissue without the need of having to use multiple needle holding instruments.

Yet another object of the present invention is to minimize the number of puncture sites required for suturing anatomical tissue in an endoscopic procedure by inserting a pair of needle holders through a single puncture site with a suturing instrument having one or more controls operable to move the needle holders relative to one another in a cooperative manner to suture anatomical tissue.

An additional object of the present invention is to permit suturing of anatomical tissue in an endoscopic procedure using a curved suture needle having a radius of curvature larger than a radial dimension of the portal through which the suturing instrument is inserted.

It is a further object of the present invention to permit a suturing instrument as well as other medical instruments and devices to be introduced through a single portal in an endoscopic procedure without the need of having to withdraw the suturing instrument from the portal.

Some of the advantages of the present invention over the prior art are that suturing of anatomical tissue can be accomplished in a time efficient, consistent and precise manner, that suturing can be accomplished using standard suture needles and filamentous suture materials without the need of having to insert additional instruments at the operative site, that single-handed suturing is made possible, that conventional handle structures can be used to provide users with a familiar feel and to decrease adaptation time, and that the instrument can be made sterilizable for reuse or disposable for single patient use as desired.

The present invention is generally characterized in an instrument for suturing anatomical tissue with a suture needle including a housing, an elongate tubular member having a proximal end mounted by the housing and a distal end with a peripheral edge, a needle driver having a distal end movable between an undeployed position where the distal end of the needle driver is disposed laterally inward of the peripheral edge of the elongate tubular member and a deployed position where the distal end of the needle driver is disposed laterally outward of the peripheral edge, and a needle catcher having a distal end movable between an undeployed position where the distal end of the needle catcher is disposed laterally inward of the peripheral edge of the elongate tubular member and a deployed position where the distal end of the needle catcher is disposed laterally outward of the peripheral edge. At least one of the needle driver and the needle catcher is coupled with the housing for arcuate movement about a longitudinal axis of the elongate tubular member such that a corresponding distal end of the at least one needle driver and needle catcher is caused to move along an arcuate path having a radius of curvature greater than the distance between the longitudinal axis and the peripheral edge of the elongate tubular member. In addition, respective distal ends of the needle driver and the needle catcher are operable to grasp and release a suture needle so that, when the needle driver and the needle catcher are in the deployed positions, a suture needle having a radius of curvature commensurate with the radius of curvature of the arcuate path can be driven through tissue using the distal end of the needle driver and subsequently transferred to the distal end of the needle catcher to be pulled through the tissue. An inner tubular member may be disposed within the elongate tubular member with a small radial clearance to define an annular space therebetween, with the needle driver and needle catcher being movably disposed within the annular space. If provided, the inner tubular member preferably extends through the housing to define a longitudinal operating passage or channel along the length of the instrument, with a valve and/or a coupling preferably being disposed at a proximal end of the operating channel to control passage of fluids and instruments through the channel.

Another aspect of the present invention is generally characterized in a method of suturing anatomical tissue using a length of suture material attached to a suture needle including the steps of grasping the suture needle with a needle driver extending outwardly from a distal end of an elongate tubular member at an angle relative to a longitudinal axis of the elongate tubular member, using the needle driver to drive the suture needle through the anatomical tissue in a first direction along an arcuate path having a radius of curvature substantially commensurate with the radius of curvature of the suture needle to cause the tip of the needle to penetrate the anatomical tissue, receiving the tip of the suture needle in a needle catcher, grasping the suture needle with the needle catcher, releasing the suture needle from the needle driver, and using the needle catcher to pull the suture needle through the anatomical tissue in the first direction along a second arcuate path having a radius of curvature substantially commensurate with the radius of curvature of the suture needle.

Yet another aspect of the present invention is generally characterized in a method of suturing anatomical tissue using a length of suture material attached to a suture needle including the steps of grasping the suture needle with a needle driver extending from a distal end of an elongate tubular member, using the needle driver to drive the suture needle through the anatomical tissue in a first direction along an arcuate path having a radius of curvature substantially commensurate with the radius of curvature of the suture needle to cause the tip of the needle to penetrate the anatomical tissue, receiving the tip of the suture needle in a needle catcher extending outwardly from the distal end of the elongate tubular member at an angle relative to a longitudinal axis of the elongate tubular member, grasping the suture needle with the needle catcher, releasing the suture needle from the needle driver, and using the needle catcher to pull the suture needle through the anatomical tissue in the first direction along a second arcuate path having a radius of curvature substantially commensurate with the radius of curvature of the suture needle.

Still another aspect of the present invention is generally characterized in a method of suturing anatomical tissue using a length of suture material attached to a suture needle including the steps of grasping the suture needle with a needle driver extending outwardly from a distal end of an elongate tubular member at an angle relative to a longitudinal axis of the elongate tubular member, using the needle driver to drive the suture needle through the anatomical tissue in a first direction along an arcuate path having a radius of curvature substantially commensurate with the radius of curvature of the suture needle to cause the tip of the needle to penetrate the anatomical tissue, receiving the tip of the suture needle in a needle catcher extending outwardly from the distal end of the elongate tubular member at an angle relative to a longitudinal axis of the elongate tubular member, grasping the suture needle with the needle catcher, releasing the suture needle from the needle driver, and using the needle catcher to pull the suture needle through the anatomical tissue in the first direction along a second arcuate path having a radius of curvature substantially commensurate with the radius of curvature of the suture needle.

Other objects and advantages of the present invention will become apparent from the following description of the preferred embodiments taken in conjunction with the accompanying drawings, wherein like parts in each of the several figures are identified by the same reference numerals or by reference numerals having the same last three digits.

BRIEF DESCRIPTION OF THE DRAWINGS

FIGS. 3 and 4 are a top view, partly in section, and a front view, respectively, of the suturing instrument of FIG. 1 with the needle driver and catcher in undeployed positions.

FIGS. 5 and 6 are a top view, partly in section, and a front view, respectively, of the suturing instrument of FIG. 1 with the needle driver and catcher in deployed positions.

FIG. 23 is a fragmentary side view of the distal end of a suturing instrument according to the present invention with a pair of modified needle holders as shown in FIG. 21 oriented to face inwardly.

FIG. 24 is a fragmentary side view of the distal end of a suturing instrument according to the present invention with a pair of modified needle holders as shown in FIG. 21 oriented to face outwardly.

FIG. 25 is a fragmentary perspective view of still another modification of a needle holder for use with the suturing instrument according to the present invention.

FIG. 26 is a fragmentary side view of the distal end of a suturing instrument according to the present invention with a pair of modified needle holders as shown in FIG. 25 oriented to face inwardly.

FIG. 27 is a fragmentary side view of the distal end of a suturing instrument according to the present invention with a pair of modified needle holders as shown in FIG. 25 oriented to face outwardly.

FIG. 28 is a fragmentary perspective view of yet another modification of a needle holder for use with the suturing instrument according to the present invention.

DESCRIPTION OF THE PREFERRED EMBODIMENTS

Figure 1:
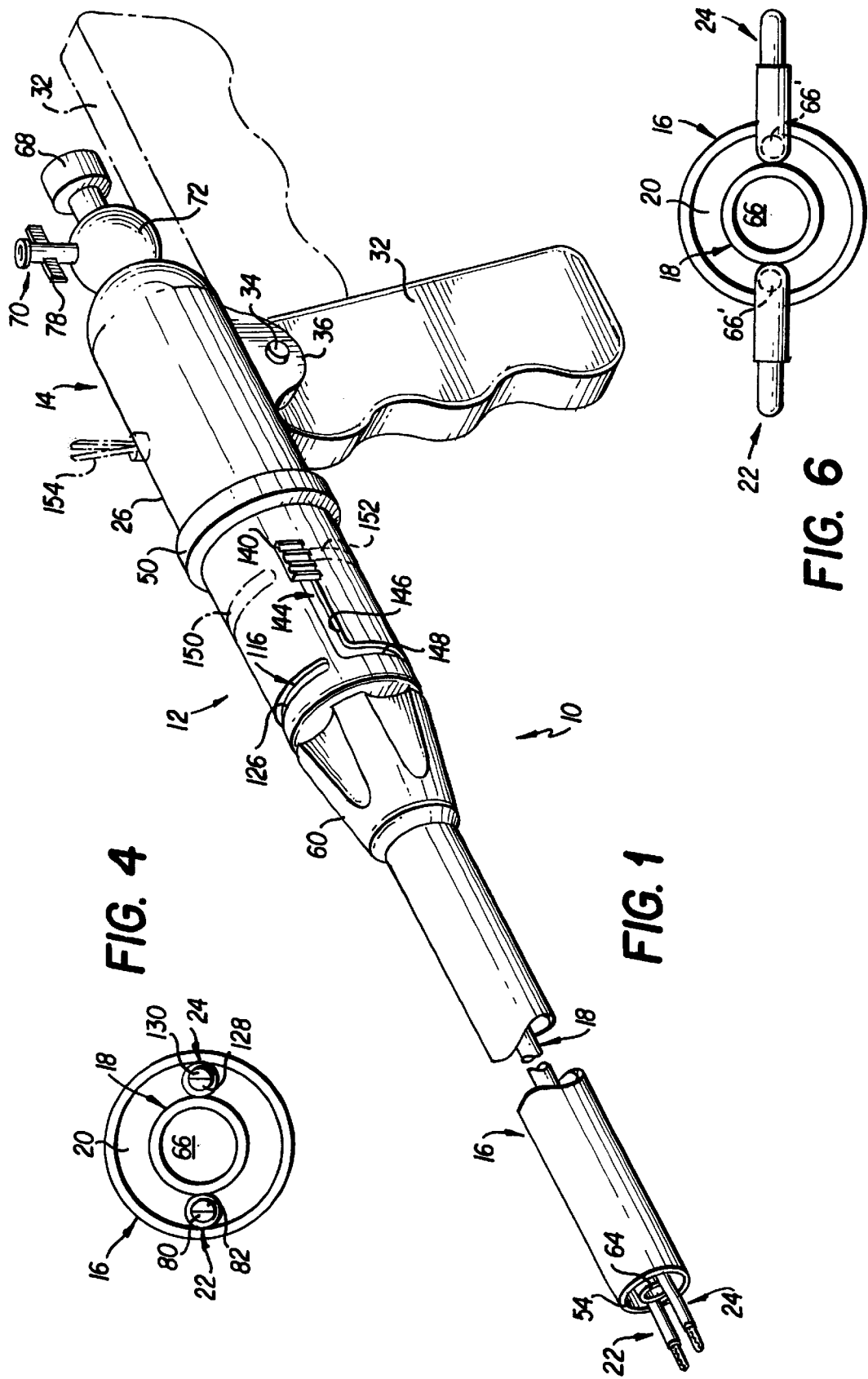
FIG. 1 is a perspective view, broken longitudinally, of a suturing instrument according to the present invention.

The suturing instrument of the present invention can be utilized to suture any type of anatomical tissue in any type of anatomical cavity; and, accordingly, while the instrument is described hereinafter for use with a portal sleeve in endoscopic procedures, such as laparoscopy, the instrument can be used in open surgery and with catheters and other small and large diameter tubular or hollow, cylindrical members providing access to small cavities, such as veins and arteries, as well as large cavities, such as the abdomen.

A suturing instrument 10 in accordance with the present invention, as illustrated in FIGS. 1–7, includes a hub or housing 12, a handle 14 coupled with a proximal end of the housing, an outer tubular member 16 extending distally from the housing, an inner tubular member 18 disposed in the outer tubular member with a small radial clearance to define an annular space 20 therebetween, and a pair of needle holders 22 and 24 movably disposed in the annular space between the inner tubular member and the outer tubular member.

Figure 2:
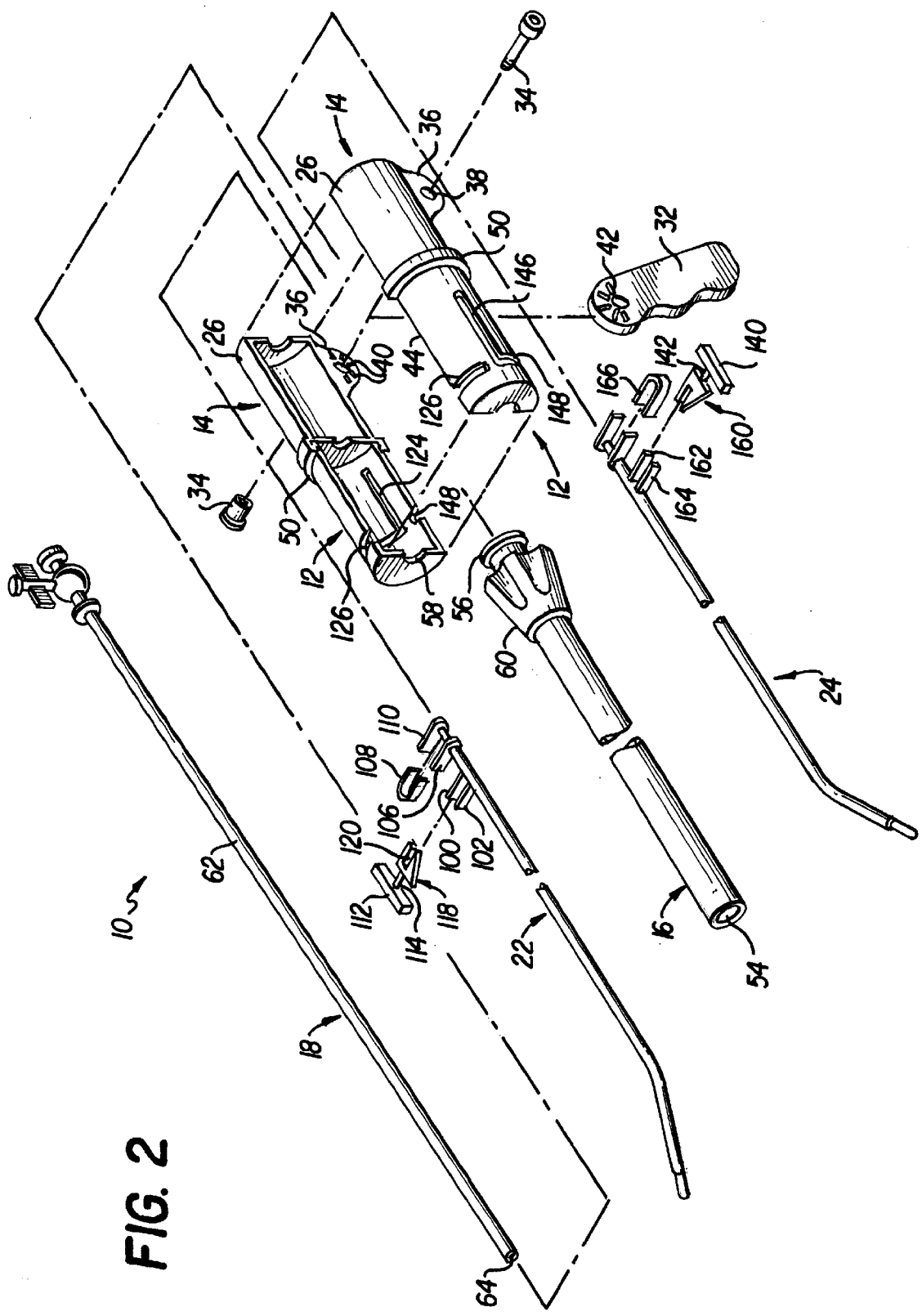
FIG. 2 is an exploded perspective view of the suturing instrument of FIG. 1.

Handle 14 includes a hollow cylindrical portion or housing 26 with longitudinally spaced front and rear walls 28 and 30 oriented perpendicular to a longitudinal axis of the inner tubular member and a pistol grip 32 pivotally mounted on a bolt or pin 34 secured between spaced, parallel flanges 36 extending outwardly from the handle housing. As best seen in FIG. 2, opposite sides of the pistol grip adjacent bolt hole 38 are each provided with one or more radial ribs or ridges 40 which extend outwardly from the pistol grip to fit within cooperatively formed grooves 42 on the inside of flanges 36 to form a detent structure allowing the pistol grip to be locked in a desired position with a ratcheting-like movement when the bolt or pin is tightened. For example, in FIG. 1, the pistol grip is shown extending transversely from the housing at an acute angle relative to the proximal direction. It will be appreciated, however, that the pistol grip can be pivoted in a counterclockwise direction (shown by broken lines in FIG. 1) or in a clockwise direction (not shown) dependent upon the procedure to be performed and the preference of the user. It is also possible to use the instrument housing as a handle, in which case a separate handle need not be attached.

Referring to FIGS. 2 and 3, housing 12 includes a hollow, cylindrical portion or side wall 44 with an open proximal end and a front wall 46 at a distal end extending perpendicular to the longitudinal axis of the outer tubular member. A groove 48 is formed about the circumference of the housing side wall adjacent the open proximal end. A cylindrical skirt or rim 50 protrudes from handle 14 in a distal direction to fit telescopically around the proximal end of housing 12 and terminates at a flange 52 which extends radially inward from the skirt or rim to be received within groove 48 to permit rotation of the handle relative to the housing. Flange 52 fits frictionally within groove 48 so that the handle can be locked in any position relative to the housing. The instrument handle and housing can be made of any substantially rigid medical grade material but are preferably formed of a plastic material of relatively high durometer to reduce weight while offering structural support for the distally extending members of the instrument.

Outer tubular member 16 is open at both ends and extends distally from housing 12 through an opening in front wall 46 of the housing. Distal end 54 of the outer tubular member can be blunt as shown, tapered, beveled, slotted or chamfered as desired or have any other distal configuration suitable for a particular procedure. Preferably, outer tubular member 16 is made of a substantially cylindrical length of a substantially rigid material, such as stainless steel or some other medically acceptable plastic or metal material. The outer tubular member terminates proximally at an outwardly extending flange 56 fixedly mounted within a recess 58 formed in the front wall of the housing such that the outer tubular member rotates with the housing. A generally frustoconical collar 60 of decreasing diameter in the distal direction extends outwardly from the outer tubular member adjacent the front wall of the housing and is configured with longitudinal fluting to facilitate manual rotation of the handle relative to the housing.

Inner tubular member 18 includes an elongate cylindrical portion 62 of hollow configuration disposed coaxially within outer tubular member 16 and having an outer diameter somewhat smaller than the inner diameter of the outer tubular member to define an annular space 20 therebetween having a radius of curvature less than the radius of curvature of the suture needle to be used. The hollow cylindrical portion 62 of the inner tubular member extends proximally from a distal end 64 aligned with distal end 54 of the outer tubular member through rear wall 30 of the handle housing to define a longitudinal operating channel or passage 66 through the instrument. The inner tubular member terminates at a coupling 68, for example a Luer lock, for connection with sources of fluid or suction, operating units, medical instruments and accessories, with a valve 70 being disposed between the hollow cylindrical portion of the inner tubular member and the coupling, the valve including a hollow spherical valve housing 72 preferably formed integrally with the inner tubular member from a substantially rigid medically acceptable plastic or metal material, and a spherical valve member 74 with a cylindrical aperture opening 76 formed therethrough rotatably disposed within the valve housing and connected with a knob 78.

Hereinafter, needle holder 22 will be referred to as a needle driver and needle holder 24 will be referred to as a needle catcher; it being understood that such designations are merely for purposes of clarity and that either needle holder can be used to drive a suture needle through anatomical tissue or to catch the end of the suture needle being driven in accordance with the present invention. Needle driver 22 and needle catcher 24 each include a pair of cooperating needle holding members mounted by the handle for rotation along arcuate paths about a longitudinal axis of the instrument, the needle holding members further being movable relative to one another to selectively grasp and release a suture needle during suturing procedures.

Needle holding members 80 and 82 defining a needle holding portion of needle driver 22 are shown as a pair of pivotably opposed jaws in FIGS. 1–17 but can have other configurations for grasping and releasing a suture needle as well as for performing other functions during a surgical procedure. Jaws 80 and 82 are preferably formed at the distal end of an elongate rod 84 of solid cross-section as an integral one-piece unit; however, it will be appreciated that the jaws can be formed separately for attachment to the rod and that the rod can be of hollow, tubular configuration to define an additional operating channel as shown, for example, by broken lines at 84' in FIG. 3 with a valve 70' and a coupling 68'. The jaws of the needle driver are biased apart toward an open position, shown at the top of FIG. 7, where inner needle holding or grasping surfaces 86 and 88 of the jaws are angularly spaced from one another. Opposed inner surfaces 86 and 88 of the jaws are shown with a plurality of longitudinally spaced teeth or ribs 90 oriented perpendicular to the longitudinal axis of the rod to securely hold a suture needle, tissue or other objects therebetween during a surgical procedure. In addition, inner surfaces 86 and x 41 are oriented to permit a suture needle having a radius of curvature to be held between the jaws of the needle driver such that the needle extends from the jaws along an arcuate path coaxial with the central longitudinal axis of the inner tubular member. Rod 84 includes a proximal portion 92 of generally straight configuration disposed within the annular space 20 between inner and outer tubular members, and a distal portion 94, to define an angled arm with a predetermined deployed shape or condition where the distal portion bends outwardly at an angle relative to the longitudinal axis of the proximal portion of the rod, the distal portion assuming the deployed shape or condition when the needle driver is in an extended position with the distal portion protruding distally beyond the distal end 54 of the outer tubular member as shown, for example, by solid lines in FIG. 5. The length and angular deflection of the distal portion of the rod are such that at least portions of jaws 80 and 82 are spaced laterally outward of a peripheral edge or diameter of the outer tubular member when the distal portion is in the deployed condition. Preferably, the distance between the axis of rotation of the needle driver and the position of needle holding surfaces 86 and 88 is approximately equal to the radius of curvature of the suture needle to be used so that the suture needle can be held between the needle holding surfaces and driven through anatomical tissue along an arcuate path having a radius of curvature commensurate with the needle radius of curvature to minimize tissue trauma. The rod is preferably formed of an elastic material, such as a spring steel, having elastic properties allowing the distal portion to bend inwardly, in a lateral direction relative to the longitudinal axis of the rod, when the rod is moved proximally relative to the outer tubular member from the extended position shown in FIGS. 5 and 6 to the retracted position shown in FIGS. 3 and 4. In the retracted position, a sufficient amount of the distal portion of the rod is disposed within the outer tubular member to cause the distal portion to assume an undeployed shape or condition where the jaws do not protrude beyond the periphery or diameter of the outer tubular member. If desired, however, the instrument can be modified to permit complete retraction of the needle driver (and/or the needle catcher) to positions where the jaws are proximally spaced from the distal end of the outer tubular member as shown by broken lines in FIG. 3.

A flexible outer member or sleeve 96 of tubular configuration fits telescopically around rod 84 and is axially movable along the length of the rod between a retracted position where a distal end 98 of the flexible sleeve is proximally spaced from the jaws and an extended position where the distal end of the flexible outer member slides over the jaws. The flexibility of sleeve 96 is such that the sleeve will preferably conform to the shape of the rod even when in the outwardly bent, deployed position. A relatively rigid flange or tongue 100 extends laterally outward from flexible sleeve 96 within the instrument housing, and a similar flange or tongue 102 extends outwardly from rod 84 through a slot 104 formed in the sleeve to be disposed distally of the sleeve tongue 100. Flexible sleeve 96 terminates proximally at a second flange 106, and a bias member 108, for example a leaf spring of generally U-shaped configuration, is held in compression between sleeve proximal flange 106 and a flange 110 mounted on the rod proximally of the sleeve proximal flange to bias tongues 100 and 102 together so that the distal end 98 of the flexible sleeve is biased to move distally relative to the rod to an extended position where the distal end of the sleeve slides over jaws 80 and 82, causing the jaws to close.

Figure 7:
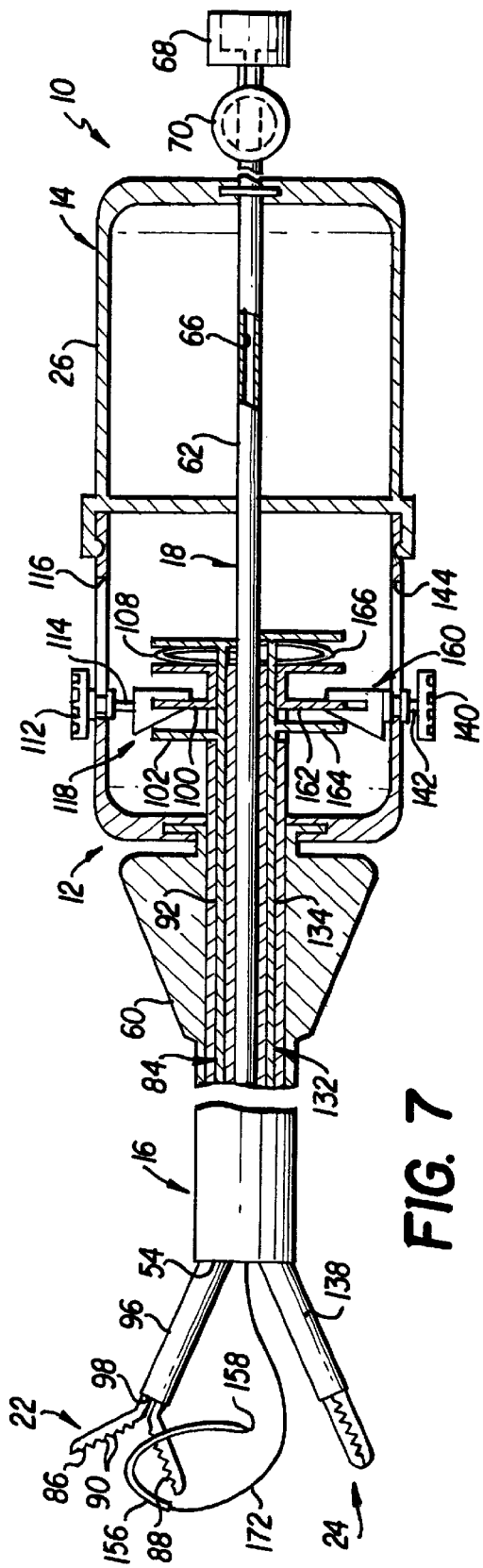
FIG. 7 is a top view, partly in section, illustrating operation of needle holding members of the needle driver.

A push button 112 is disposed externally of the instrument housing and is mounted on a plunger or post 114 which extends from the button through a slot 116 in the housing to a wedge 118 disposed within the housing. The wedge defines a slot or groove 120 for receiving tongue 100 and has a width of decreasing dimension in a laterally inward direction to define an angled distal face or cam surface 122 which acts on tongue 102 to spread tongues 100 and 102 apart when the button is in a depressed position or condition, as shown at the top of FIG. 7, and to maintain contact with tongue 100 when in an elevated or non-depressed position or condition, as shown in FIGS. 3 and 5, such that movement of the push button along the slot will cause the wedge to impart movement to the needle driver as a whole. Push button 112 is preferably of a known type which will alternatingly extend the plunger inwardly and retract the plunger outwardly in response to repeated depression. In addition, it is preferred that a portion of the push button mechanism slide frictionally within the slot 116 so that, once the push button has been moved to a desired position along the slot, the push button will not move until forced deliberately by the user. As best seen in FIGS. 1 and 2, slot 116 includes a longitudinal portion 124 oriented parallel to a longitudinal axis of the housing and a transverse portion 126 extending perpendicularly from a distal end of the longitudinal slot portion in a clockwise direction looking proximally, the transverse portion extending about a third of the way around the circumference of the housing.

Needle catcher 24 is shown as being identical to needle driver 22, with needle holding members 128 and 130 in the form of opposed jaws mounted at the distal end of a rod 132 having straight and angled portions 134 and 136 slidably disposed within a sleeve 138. It will be appreciated, however, that the needle catcher can have any configuration for holding a needle and performing other operations. Push-button 140, which controls operation of the needle catcher, is similar to push-button 112 with a plunger or post 142 extending therefrom through a slot 144 formed in the housing in circumferentially spaced relation to slot 116. As best seen in FIGS. 1 and 2, slot 144 is similar to slot 116, with a longitudinal portion 146 parallel to the longitudinal portion of slot 116 and spaced about 180° therefrom, and a transverse portion 148 extending circumferentially from a distal end of longitudinal slot portion 146 in a clockwise direction, looking proximally, to a position adjacent slot 116. Slots 116 and 144 may also include proximal transverse portions as shown, for example, by broken lines in FIG. 1 at 150 and 152, to permit arcuate rotation of one or both needle holders in axially retracted positions as shown and described in U.S. patent application Ser. No. 08/758,648, filed Nov. 27, 1996, the disclosure of which was incorporated hereinabove by reference. Also, while needle driver 22 and needle catcher 24 are both shown as bending outwardly of the periphery of outer tubular member 16 in their respective deployed positions, it will be appreciated that one or both of the needle driver and the needle catcher can remain straight, as shown by broken lines in FIG. 5, or bend slightly to be disposed within the periphery of the outer tubular member when extended distally dependent upon procedural use and other considerations such as the shape of the suture needle.

An electrical connector can optionally be mounted on the handle 14, as shown by broken lines at 154 in FIG. 1, or at any other suitable location on the instrument including, but not limited to, the side of instrument housing 12 or the proximal end of inner tubular member 18 adjacent valve 70, to connect electrically conductive elements of the instrument with a source of electricity for performing unipolar or bipolar procedures such as electric coagulation, for example using one or both of the jaws of a needle holder as conductive elements. In addition, an interior surface of the operating channel 66 can be coated with an electrical and/or thermal insulating layer to permit safe insertion of electrical, thermal and/or other types of energy transmitting devices through the operating channel.

In use, instrument 10 is grasped using pistol grip 32 and, in the case of an endoscopic procedure, the instrument is guided to the operative site by a portal sleeve positioned in the wall of an anatomical cavity. The portal sleeve can be positioned in the anatomical cavity wall using any suitable penetrating technique, including those creating puncture sites by means of removable obturators, such as trocars, and can include a valve housing, if desired, to prevent loss of pneumoperitoneum during insertion and withdrawal of the instrument. Visualization of the endoscopic procedure can be accomplished using a conventional endoscope incorporated into the instrument, for example within the longitudinal operating channel 66 defined by tubular shaft 62, or separately positioned within the anatomical cavity through a second portal sleeve located at another puncture site.

Prior to insertion, instrument 10 is preferably in the position shown in FIGS. 1 and 3. More specifically, needle driver 22 and needle catcher 24 are preferably initially tip positioned at diametrically opposed locations within annular space 20, for example by sliding push buttons 112 and 140 counterclockwise, looking proximally, within transverse slot portions 126 and 148 until posts 114 and 142 are disposed within longitudinal slot portions 124 and 146 and then sliding the push buttons proximally along the longitudinal slot portions until the posts abut respective proximal ends of slots 116 and 144. Needle driver 22 and needle catcher 24 should then be in retracted positions with their jaws spaced laterally inward of the peripheral edge of the outer tubular member in an undeployed condition so as not to snag or catch on structure within the portal sleeve or valve housing during insertion. To this end, push buttons 112 and 140 are preferably initially disposed in the elevated positions shown in FIG. 3 so that each of the needle holders will be in the closed or grasping position with inner grasping surfaces of the jaws close together or abutting one another.

After insertion, needle driver 22 and needle catcher 24 are preferably moved distally relative to outer tubular member 16 from the retracted, undeployed positions shown in FIGS. 3 and 4 to the extended, deployed positions shown in FIGS. 5 and 6 by sliding buttons 112 and 140 distally along longitudinal slot portions 124 and 146. As the needle holders are advanced longitudinally, distal portions of the needle holders will no longer be restrained within the outer tubular member and will thus tend to bend outwardly, away from the longitudinal axis of the outer tubular member, toward deployed positions where the jaws of each of the needle holders are spaced laterally outward of the peripheral edge of the outer tubular member. It is also possible for one of the needle holders to bend outwardly in the extended position while the other needle holder remains within the periphery of the outer tubular member as shown, for example, by broken lines in FIG. 5.

Figure 8:
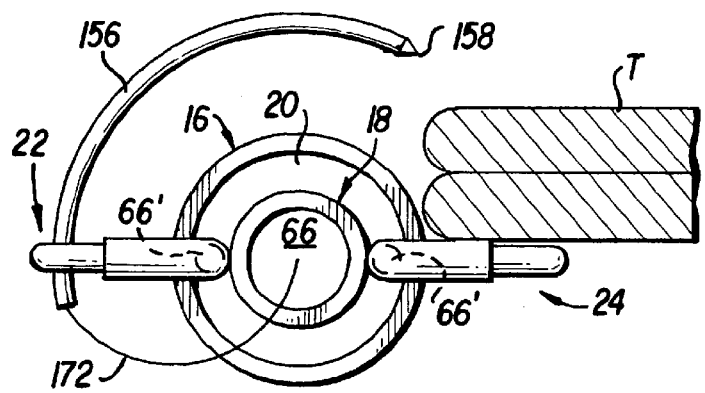
FIGS. 8–12 are front views of the suturing instrument of FIG. 1 illustrating use of the instrument for suturing anatomical tissue with a curved suture needle.

A curved suture needle 156, preferably having a radius of curvature commensurate with the distance between the axis of rotation of the needle holders and the deployed position of the needle holders, is positioned in needle driver 22 by moving jaws 80 and 82 apart from the closed position shown in FIG. 5 to the open position shown in FIG. 7, placing the body of the suture needle in the space between the jaws, and moving the jaws toward the closed position until grasping surfaces 86 and 88 abut the suture needle to hold it firmly in place. Jaws 80 and 82 are moved to the open position by depressing the push button 112 to cause the wedge 118 to spread tongues 100 and 102 apart against the influence of bias member 108, as shown in FIG. 7, such that distal end 98 of the sleeve 96 is moved proximally relative to the jaws. The body of needle 156 is then placed between grasping surfaces 86 and 88 of the needle driver with the sharp, tissue penetrating tip 158 of the needle being circumferentially aligned with, and angularly spaced from, the jaws of needle catcher 24. With needle 156 positioned within jaws 80 and 82 of needle driver 22, push button 112 on the side of the instrument corresponding to the needle driver is depressed to cause the wedged-shaped terminal end 118 to elevate or move away from tongues 100 and 102 so that the tongues can move together under the influence of bias member 108. Movement of tongue 100 towards tongue 102 causes distal end 98 of sleeve 96 to move distally relative to rod 84 and into camming contact with jaws 80 and 82, causing the jaws to move toward one another and into gripping contact with the body of needle 156 as shown in FIG. 8. Needle 156 is thus held securely between jaws 80 and 82 and will move with needle driver 22 during the suturing procedure.

Needle catcher 24 is configured to receive the tip of the suture needle by moving jaws 128 and 130 to the open position prior to, during or after the suture needle has been loaded in needle driver 22. This can be accomplished by depressing the push button 140 to cause the wedge 160 at the terminal or inner end of plunger or post 142 to spread tongues 162 and 164 apart against the influence of bias member 166 such that distal end 168 of the sleeve 170 moved proximally relative to jaws 128 and 130.

Figure 9:
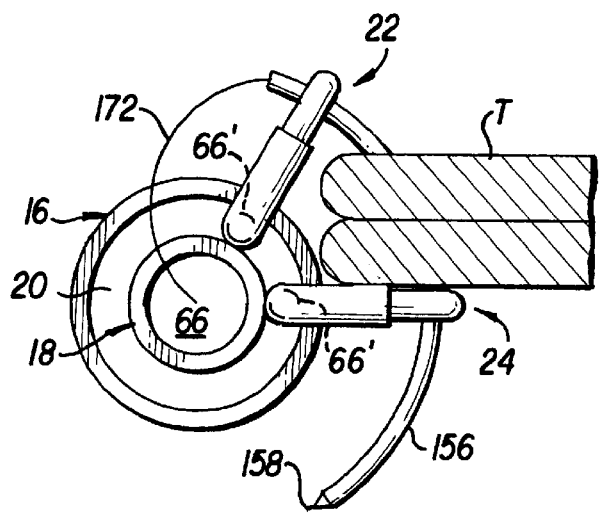

Referring now to FIG. 8, anatomical tissue T is positioned between tip 158 of needle 156 and the needle catcher 24 with a length of filamentous suture material 172 being shown attached to the proximal end of the needle for purposes of illustration only. Using the open needle catcher 24 as a backing or support for the tissue, the needle is driven through tissue T and into the needle catcher by rotating knob 112 in a clockwise direction, looking proximally, along transverse slot portion 126 until post 114 abuts the opposite terminal end of the transverse slot portion or needle driver 22 abuts the tissue being sutured. Tip 158 of needle 156 is thus caused to penetrate through the anatomical tissue T and into the space between open jaws of needle catcher 24 along an arcuate path having a radius of curvature approximately equal to or commensurate with the radius of curvature of the needle until the tip is disposed at a location spaced clockwise from the needle catcher as shown in FIG. 9. During rotation of needle driver 22, it will be appreciated that wedge 118 maintains the radial or outward orientation of tongues 100 and 102 while preventing the tongues from becoming spread apart, thus maintaining grasping pressure on the suture needle.

With needle 156 positioned between grasping surfaces of the needle catcher jaws 128 and 130, push button 140 on the side of the instrument corresponding to needle catcher 24 is depressed to cause the plunger to be retracted thereby permitting tongues 162 and 164 of the needle catcher 24 to move together under the influence of bias member 166 and causing distal end 168 of the flexible sleeve to slide over the jaws. Jaws 128 and 130 are thus moved toward the closed position where they contact the body of the suture needle to securely grasp the needle. Button 112 on the side of the instrument corresponding to needle driver 22 may then be depressed to extend the plunger and cause tongues 102 and 100 to move apart, thereby moving the distal end 98 of the sleeve 96 proximally relative to jaws 80 and 82 so that the jaws move toward the open position thereby releasing the suture needle.

Figure 10:
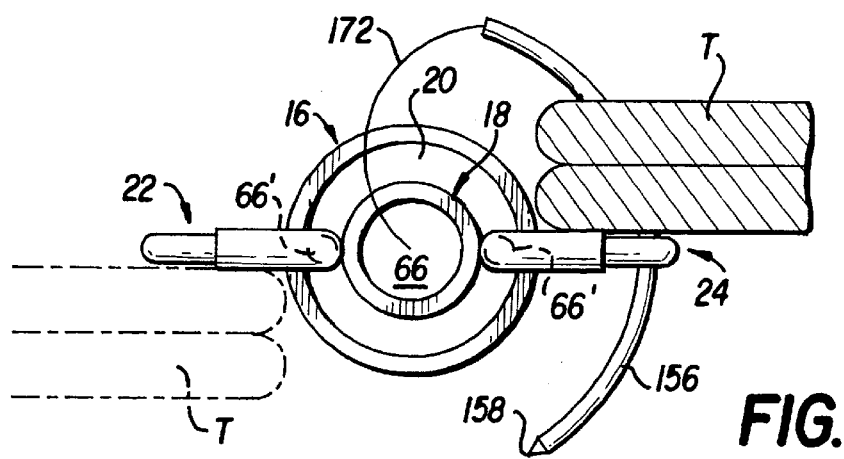
Figure 11:
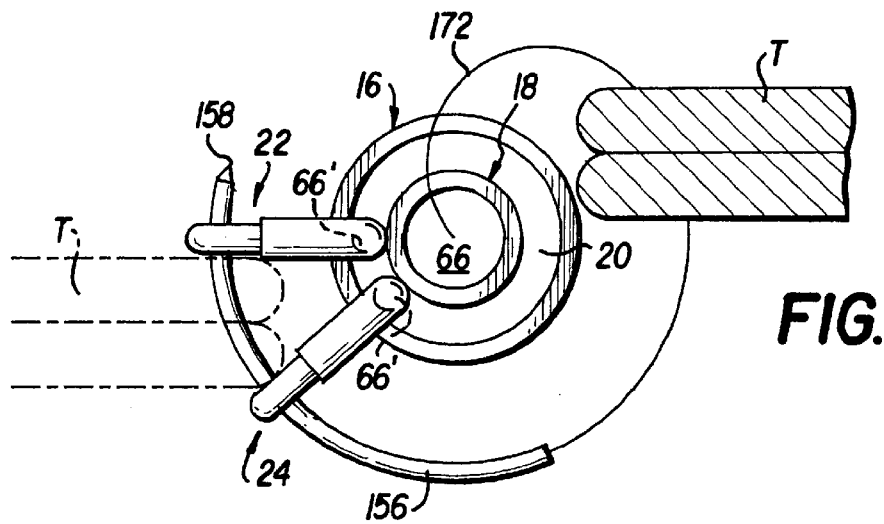
Figure 12:
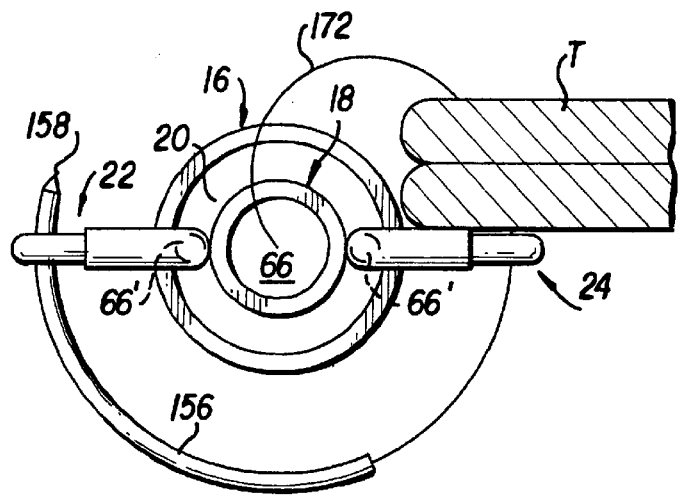

With needle 156 secured within the jaws of needle catcher 24, knob 140 is rotated clockwise, looking at FIG. 10, until post 142 abuts a terminal end of circumferential or transverse slot portion 148 and the tip of needle 156 extends into the path of movement of needle driver 22 as shown in FIG. 11. Suture needle 156 is thus pulled through the anatomical tissue with the length of suture material 172. At this point, the length of suture material can be knotted to form a single stitch or another stitch can be made by driving the suture needle through the anatomical tissue at a second site or location using the needle catcher or the needle driver. In the case of another stitch being made using the former technique, the instrument is moved away from the tissue to permit the needle driver and the needle catcher to be moved to the positions shown in FIG. 10, after which the instrument is manipulated to position the tissue T between the needle catcher and the needle holder in the path of rotation of the suture needle as shown by broken lines in FIG. 10. The needle catcher is then rotated clockwise, looking at FIG. 10, to cause the suture needle to penetrate through the tissue as shown by broken lines in FIG. 11. The suture needle may then be grasped by the needle driver and released from the needle catcher to be pulled completely through the tissue with clockwise rotation of the needle driver, looking at FIG. 11. In the case of another stitch being made using the latter technique, needle driver knob 112 is rotated in a counterclockwise direction about 180°, looking at FIG. 9, to receive the tip of suture needle 156 as shown in FIG. 11. At this point, the needle driver push button 112 is depressed to elevate the plunger so that suture needle 156 is secured between the jaws 80 and 82 of the needle driver and, at about the same time, needle catcher push button 140 is depressed to cause the plunger to lower thereby releasing the suture needle from the needle catcher. A second stitch is then made by moving suturing instrument 12 slightly relative to tissue T and rotating needle driver rotation knob 112 clockwise, looking at FIG. 10, to cause tip 158 of suture needle 156 to penetrate through the tissue at a second location, the suture needle having now made two complete revolutions about the axis of rotation of the needle holders. Needle catcher 24 has preferably previously been rotated in a counterclockwise direction, looking at FIG. 12, by rotation of the needle catcher operating button 140 along circumferential slot portion 148 to receive the suture needle, after which needle catcher operating button 140 is elevated to secure suture needle 156 within the needle catcher. At about the same time, the needle driver operating button 112 is depressed to permit the suture needle to be pulled completely through the tissue by clockwise rotation of the needle catcher 24. At some point, the suture needle 156 may need to be advanced circumferentially in the clockwise direction in order for the tip 158 to protrude sufficiently from the needle driver for additional stitches to be formed. Such repositioning can, for example, be accomplished by grasping the proximal end of the needle with the needle catcher or a separate needle holding instrument and releasing the needle holding members of the needle driver to allow manipulation of the needle to a position in the needle driver wherein the tip of the needle protrudes sufficiently to pass through the anatomical tissue and be captured by the needle catcher.

Figure 13:
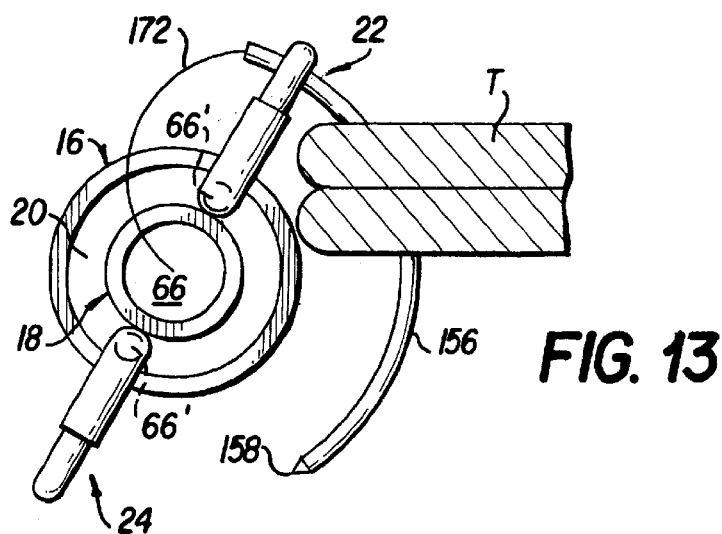
FIGS. 13–16 are front views of the suturing instrument of FIG. 1 illustrating another way of using the instrument to suture anatomical tissue with a curved suture needle.
Figure 14:
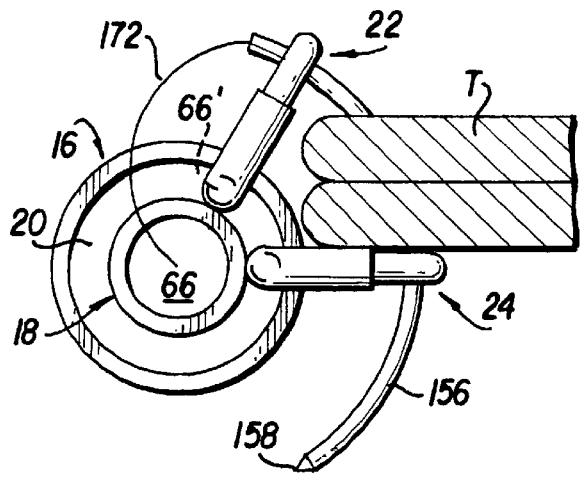
Figure 15:
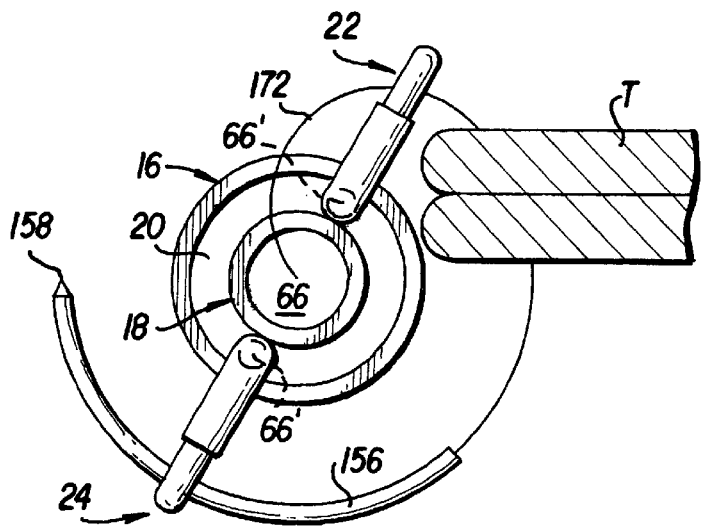
Figure 16:
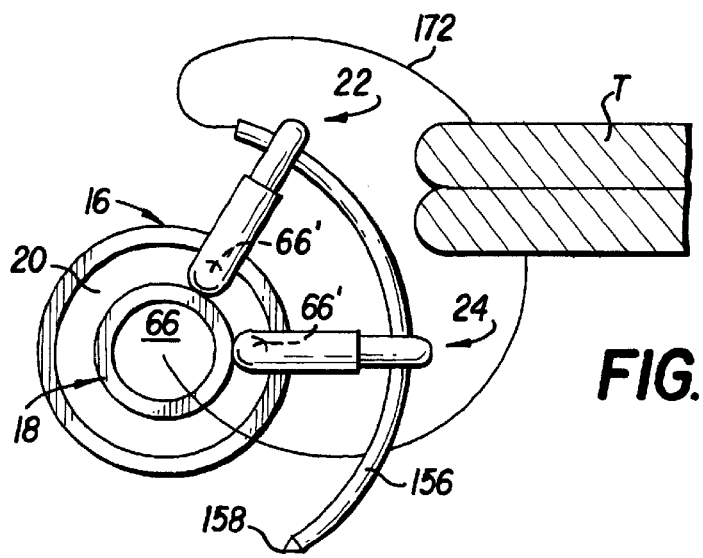

The suturing instrument can also be used to suture anatomical tissue in the manner shown in FIGS. 13–16 wherein the needle driver 22 and the needle catcher 24 are initially diametrically opposed as shown in FIG. 8, for example by positioning the needle driver and the needle catcher at respective terminal ends of transverse slot portions 126 and 148. The instrument housing 12 is then rotated in a clockwise direction, looking at FIG. 6, about the longitudinal axis of the outer tubular member, for example by rotating handle 14 with a twisting movement of the user's wrist and allowing the instrument housing to rotate with the handle, to drive the suture needle 156 through the anatomical tissue in a clockwise direction as shown in FIG. 13 along an arcuate path having a radius of curvature substantially commensurate with the radius of curvature of the needle. Needle catcher 24 is also moved along an arcuate path in a clockwise direction about the longitudinal axis of the outer tubular member as the instrument housing is rotated and may need to be moved counterclockwise, looking at FIG. 13, in an arcuate manner to receive the body or tip of the suture needle while holding the needle driver substantially stationary as shown in FIG. 14. The needle catcher 24 is then operated to grasp the tip of the suture needle at about the same time the needle driver 22 is operated to release the suture needle, thereby transferring the suture needle to the needle catcher and allowing the suture needle to be pulled through the anatomical tissue by clockwise rotation of the needle catcher about the longitudinal axis along an arcuate path as shown in FIG. 15. The instrument may then be moved away from the anatomical tissue slightly so that the suture needle can be transferred back to the needle driver by arcuately rotating the needle catcher in the counterclockwise direction, looking at FIG. 15, until the proximal end or body of the suture needle is received by the needle driver as shown in FIG. 16. Needle catcher 24 is operated to release the suture needle at about the same time needle driver 22 is operated to grasp the suture needle, the needle catcher then being arcuately rotated in a clockwise direction, looking at FIG. 16, to the initial position shown in FIG. 13 so that the suturing instrument can be used to apply another stitch to the anatomical tissue in the manner described above.

At any point during the surgical procedure, operating channel 66 of the suturing instrument can be used for irrigation or aspiration of the surgical site and can serve as a space for holding the suture material or as a portal for the introduction of other medical instruments and devices such as, for example, forceps, cutting members, needles and endoscopes. Knotting elements can also be introduced at the operative site via the operating channel for use in lieu of or in addition to traditional knotting techniques during the suturing procedure. Some examples of suitable knotting elements for this purpose are described in pending applications Ser. Nos. 08/366,285, filed Dec. 29, 1994; 08/377,723, filed Jan. 25, 1995; 08/401,002, filed Mar. 9, 1995; and 08/585,875, filed Jan. 16,1996; the disclosures of which are incorporated herein by reference.

Figure 17:
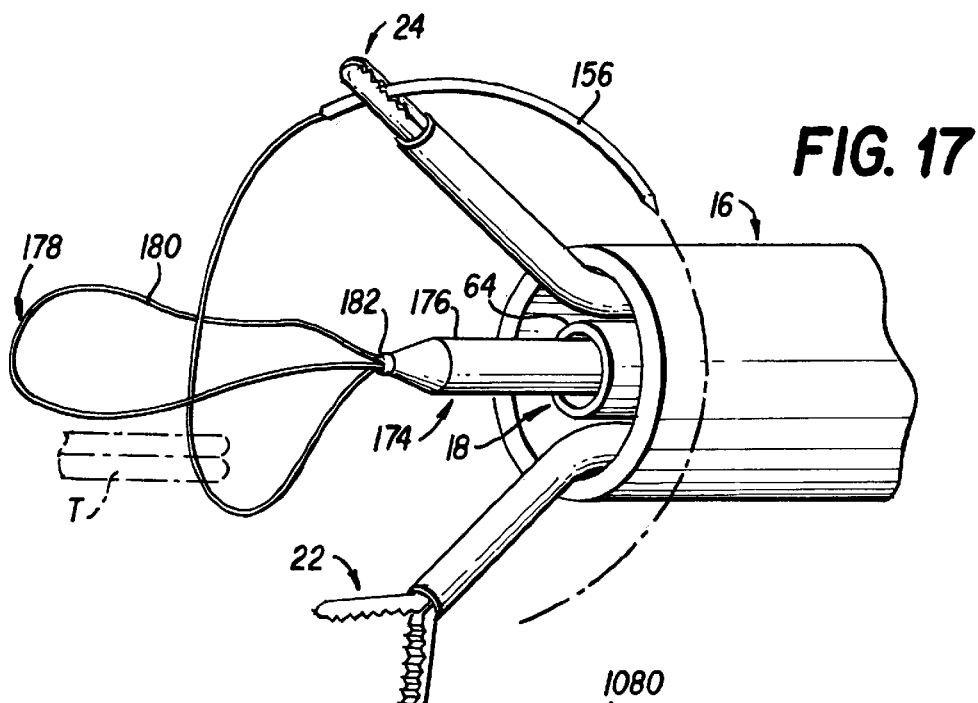
FIG. 17 is a fragmentary perspective view of the suturing instrument according to the present invention with a ligating device inserted therethrough.

FIG. 17 illustrates a further use of operating channel 66 wherein a ligating device 174 is advanced distally through the channel to assist in tying a suture. The device 174 is of the conventional ENDOLOOP-type and includes an elongate tubular pusher 176 and a length of filamentous ligature material 178 extending through the pusher to define a loop 180 with a knotting element 182 in the form of a pretied knot at the distal end of the pusher. For purposes of illustration, a free end of the ligature material is shown attached to the proximal end of suture needle 156 so that, after the suture needle has been pulled through anatomical tissue with the ligature material, the needle can be passed through the loop and the loop can be tightened to control the tension of the suture.

In addition to the main operating channel 66, auxiliary operating channels can be defined through one or both of the needle driver 80 and the needle catcher 82 as shown by broken lines at 66' in FIGS. 8–16 to provide access to the operative site from outside the anatomical cavity. The auxiliary operating channels can terminate distally at openings adjacent the jaws of the needle driver and the needle catcher or at openings defined at the bend connecting straight and angled portions of the needle driver and the needle catcher.

Figure 18:
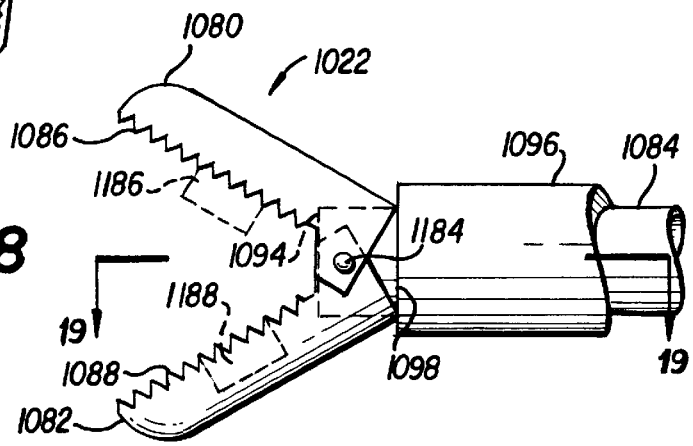
FIG. 18 is a fragmentary side view of a modified needle holder for use with the suturing instrument according to the present invention.
Figure 19:
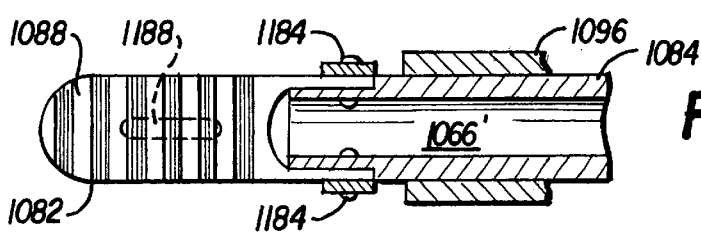
FIG. 19 is a cross-sectional view of the modified needle holder taken through line 19—19 in FIG. 18.

FIGS. 18 and 19 show a modification of a needle holder 1022 for use with the suturing instrument according to the present invention wherein the modified needle holder 1022 includes a pair of jaws 1080 and 1082 pivotably mounted on a pair of pins 1184 secured to diametrically opposed sides of a hollow tubular rod or sleeve 1084 telescopically fitted within an outer tubular sleeve 1096, the tubular rod defining an auxiliary operating channel 1066' providing access to the operative site from outside the anatomical cavity. Jaws 1080 and 1082 are biased apart toward the open position shown in FIG. 18, for example using a torsion spring (not shown) coiled around one of the pins and connected between the jaws or a pair of spring members (not shown) held in compression between each jaw and the hollow tubular rod, and the jaws are movable inwardly toward one another against the spring bias in response to distal movement of outer tubular sleeve 1096 against the rear or back edges of the jaws.

Any of the needle holding members described herein can carry a biopsy box or a cutting member such as the blade shown by broken lines at 1186 in FIG. 18. Blade 1186 is oriented perpendicular to inner surface 1086 of the upper jaw 1080 and extends inwardly from the inner surface to fit within a cooperatively configured pocket or recess 1188 formed in lower jaw 1082 when the jaws are closed together. Examples of other cutting members which can be used are shown and described in U.S. patent applications Ser. No. 08/61 2,634, filed Mar. 4, 1996, and U.S. Ser. No. 08/376, 186, filed Jan. 20, 1995, the disclosures of which are incorporated herein by reference.

Figure 20:
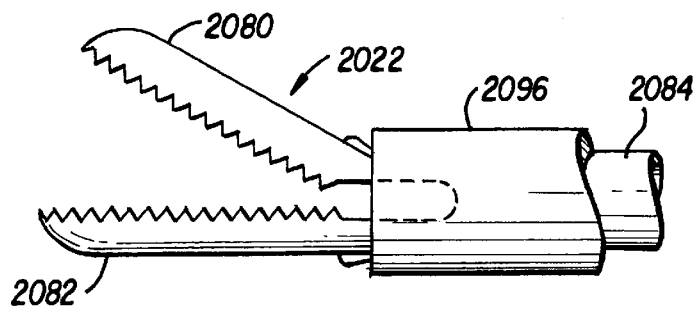
FIG. 20 is a fragmentary side view of another modification of a needle holder for use with the suturing instrument according to the present invention.

The modified needle holder 2022 shown in FIG. 20 is similar to the needle holders shown in FIGS. 1–14 but with a hollow, tubular rod or sleeve 2084 of generally cylindrical configuration defining an operating channel 2066' along the length of the needle holder and a pair of jaws 2080 and 2082 formed integrally with the hollow tubular rod as a one-piece unit. The lower jaw 2082 in FIG. 20 is of fixed configuration and extends in parallel with a longitudinal axis of the hollow tubular rod while the upper jaw 2080 is pivotably movable between an open position extending outwardly from the tubular rod longitudinal axis at an angle and a closed position abutting the lower jaw. If desired, the fixed jaw can be formed integrally with the tubular rod and the movable jaw can be pivotably mounted on one or more pins as shown, for example, in FIGS. 18 and 19.

Figure 22:
FIGS. 21 and 22 are a fragmentary side view and a front view, respectively, of another modified needle holder for use with the suturing instrument according to the present invention.
Figure 21:
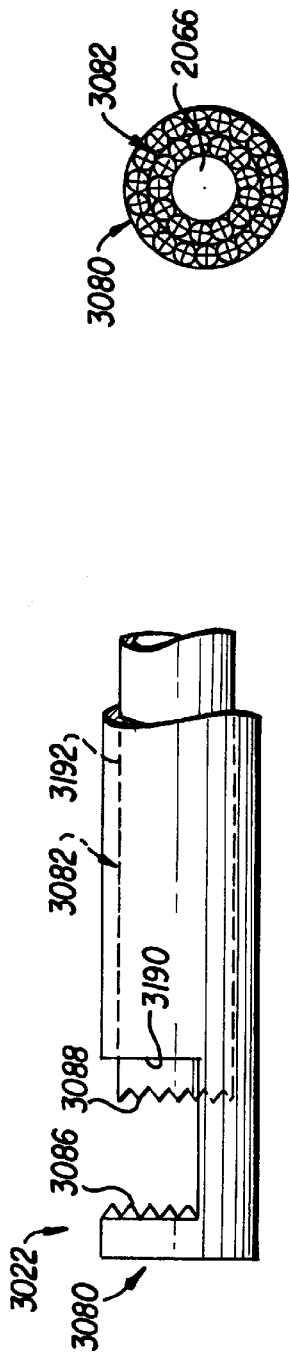

Yet another modified needle holder is shown in FIGS. 21 and 22 at 3022 and includes a first needle holding member in the form of an outer tubular sleeve 3096 with a lateral cut-out or window 3190 having a grasping surface 3086 formed along a proximal-facing peripheral edge of the window and a second needle holding member in the form of an inner tubular sleeve 3192 fitted telescopically within the outer tubular sleeve and having a grasping surface 3088 formed along a distal peripheral edge of the inner sleeve to operate cooperatively with the grasping surface of the window to hold a suture needle or other objects within the window while permitting access to the operative site via the channel defined by the inner tubular sleeve.

The window 3190 in the outer tubular sleeve 3096 of the modified needle holder 3022 can be oriented to face any suitable direction relative to the central longitudinal axis of the outer tubular member of the suturing instrument dependent upon the shape of the suture needle or procedural use. For example, in FIG. 23, a pair of needle holders 3022 and 3024 identical to the needle holder shown in FIGS. 21 and 22 are oriented such that their respective windows 3190 and 3206 face inwardly, toward the central longitudinal axis of the suturing instrument. By directing the windows inwardly, the process of loading a suture needle into one of the needle holders from the central operating channel 66 can be simplified. In FIG. 24, on the other hand, needle holders 3022 and 3024 are oriented such that their respective windows 3190 and 3206 face outwardly, away from the central longitudinal axis of the suturing instrument.

FIG. 25 shows still another modification of a needle holder for use with the suturing instrument according to the present invention wherein the modified needle holder 4022 includes a first needle holding member 4080 in the form of a hook and a second needle holding member 4082 in the form of a keeper movable relative to the hook to capture and release a suture needle placed within the hook. The needle holding members are preferably formed of flat strips of a medically acceptable material, such as stainless steel, configured to lay flat against one another to permit relative sliding movement of the needle holding members. The first needle holding member 4080 includes an elongate portion or leg 4194 extending distally from within the instrument housing to a bend 4196 where the first needle holding member folds inwardly upon itself to form a short leg 4198 parallel to the elongate portion or leg of the needle holding member thereby defining a hook with a proximal-facing mouth having a gap width suitable for receiving the shaft or body of a suture needle. The second needle holding member 4082 is slidingly disposed along the first needle holding member 4080 and includes a distal end 4200 configured to fit within the mouth of the hook as a keeper, the distal end of the second needle holding member being shown with an optional scalloped edge having one or more curved recesses. The first or second needle holding member may also be formed with a cutting member such as a blade or a notch of generally V-shaped configuration defined along an edge of the needle holding member and having one or more sharp edges to cut lengths of suture material received therein under pressure. The first needle holding member is also shown with optional slots or openings 4202 and 4204 formed on opposite sides of the hook to permit straight or slightly curved suture needles to be placed perpendicularly through short and long legs of the hook so as to be oriented radially relative to the longitudinal axis of the inner tubular member. The slotted openings extend transversely, relative to a longitudinal axis of the needle holder, from respective open ends disposed along a lateral or longitudinal edge of the first needle holding member to generally centrally located terminal ends of rounded or semicircular configuration with a size to receive the body or shank of a suture needle extending transversely through legs of the hook. As mentioned above, the scalloped edge at the distal end of the second needle holding member or keeper 4082 is configured with laterally spaced recesses, one of which is preferably aligned with the terminal portion or end of the slotted openings to cradle a needle positioned within the openings in a manner to secure the needle during laterally inward and outward suturing procedures performed as described in U.S. patent application Ser. No. 08/758,648, filed Nov. 27, 1996, the disclosure of which was incorporated by reference hereinabove.

The hook-like needle holding member shown in FIG. 25 can be positioned within the annular space between the inner and outer tubular members of the suturing instrument such that the mouth of the hook formed at the distal end of the needle holding member opens inwardly as shown, for example, in FIG. 26, or outwardly, as shown in FIG. 27, dependent upon procedural use and the shape or radius of curvature of the suture needle. In the former case, the keeper is disposed between the hook-like member and the inner tubular member while in the latter case, the keeper is disposed between the hook-like member and the outer tubular member of the instrument.

Another modification of the suturing instrument according to the present invention is shown in FIG. 28 wherein the modified suturing instrument 5010 includes a pair of needle holders 5022 and 5024 (the latter of which is shown by broken lines for purposes of clarity) similar to those shown in FIG. 25 but with needle holding members 5080 and 5082 of greater circumferential width having a curvature substantially commensurate with the radius of curvature of the suture needle to provide additional support for the body of the suture needle while still being able to slide conformally within the annular space between inner and outer tubular members 18 and 16.

From the above, it will be appreciated that the suturing instrument according to the present invention permits suturing of anatomical tissue during endoscopic procedures without the need of having to use multiple needle holding instruments inserted through multiple puncture sites by inserting a needle driver and a needle catcher through a single puncture site with a suturing instrument having an elongate tubular member and one or more controls at a proximal end of the elongate tubular member operable to move the needle driver and the needle catcher relative to one another along arcuate paths in a cooperative manner to suture the anatomical tissue. The needle driver and the needle catcher each include needle holding members selectively operable to grasp and release a suture needle so that, when the needle holding members of the driver are operated to grasp the suture needle, the driver can be moved in a direction to drive the suture needle through anatomical tissue positioned between the driver and the catcher, and when the needle holding members of the catcher are operated to grasp the suture needle, the needle holding members of the driver can be operated to release the suture needle, thereby allowing the catcher to be moved in a direction to pull the suture material through the anatomical tissue. In addition, at least one of the needle driver and the needle catcher is movable between an undeployed, contracted or parked position where respective needle holding members are spaced laterally inward of a peripheral edge of the elongate tubular member and a deployed, expanded or working position where the needle holding members are spaced laterally outward of the peripheral edge of the elongate tubular member so that suturing of anatomical tissue can be accomplished using a suture needle having a radius of curvature larger than a radial dimension of the elongate tubular member (in the event the tubular member is of circular cross-section) or the distance between the axis of rotation of the needle holding members and the peripheral edge of the elongate tubular member (in the event the tubular member is of circular or non-circular cross-section).

The needle driver and the needle catcher of the suturing instrument can be of the same design or of different designs so long as each includes a needle holder capable of grasping and releasing a needle. The needle holders can be configured to hold any type of needle including, but not limited to, straight and curved needles, and are preferably mounted to permit movement of the needle holders relative to one another in directions causing the needles to be passed from one needle holder to the other. In the case of curved needles, the needle holders are preferably mounted for rotation about a longitudinal axis of the suturing instrument in an arcuate path having a radius of curvature commensurate with the radius of curvature of the needle. Alternatively, at least one of the needle holders can be mounted for rotation about its own longitudinal axis such that distal ends of the needle holders are caused to move along non-concentric arcuate paths which may or may not intersect dependent upon the configuration of the needle holders. For straight needles, one or both of the needle holders is preferably pivotable away from a longitudinal axis of the suturing instrument and the needles are preferably held by the needle holders such that tissue penetrating tips of the needles are oriented toward the longitudinal axis of the instrument. One or more lengths of suture material can be attached to each suture needle at any desirable location along the body of tip of the needle including, but not limited to, the proximal end of the needle, intermediate or medial portions of the needle body, or locations adjacent the tip of the needle. It will also be appreciated that the suturing instrument according to the present invention can be used with any type of standard suturing needle including, but not limited to, needles having sharp or blunt tissue penetrating tips, and needles having tissue penetrating tips at opposite axial ends of a needle body.

The needle holding members of the needle catcher and the needle driver shown and described herein are exemplary of the types of needle holding members that can be used according to the present invention. Accordingly, the needle holding members can have any suitable configuration for cooperatively grasping needles to suture anatomical tissue including, but not limited to, configurations wherein the needle holding members pivot, slide or otherwise move relative to one another to capture and release a needle. The needle holding members can be of straight, curved or angled configuration and can be provided with ribs, grooves, slots and/or holes along grasping surfaces to assure a positive grip. The needle holding members can also carry cutting members, such as slots with sharp edges or protruding blades, and can have opposed arcuate or concave portions for clamping tubular objects, such as organs, without compressing the objects, as well as portions configured to take a tissue sample for biopsy.

The needle driver and catcher of the present invention are preferably movably disposed about a tubular member defining one or more operating channels or passages through the instrument to permit various medical devices and instruments such as, for example, needles, blades, forceps, cauteries, endoscopes, illuminating devices and lengths of suture material to be introduced at the operative site without the need of having to remove the suturing instrument from the body. The tubular member defining the operating channel can have any configuration in transverse cross-section including, but not limited to, elliptical, polygonal and irregular or asymmetrical cross-sectional configurations. Also, all or part of the inner surface of the tubular member can be electrically insulated to permit passage of electrosurgical instruments therethrough. The valve and coupling shown at the proximal end of the tubular member are merely exemplary of the types of conventional valves and conventional couplings that can be used. Operating channels may also be defined along the length of the needle driver and the needle catcher of the instrument, if desired.

The needle driver and catcher of the present invention can also be used alone or in combination as end effectors to perform lysis of adhesion; pickup, clipping and cutting of tissue and other objects; unipolar and bipolar electrosurgery; and numerous other procedures. Although the suturing instrument is shown and described herein as having two needle holders, it will be appreciated that one or more than two needle holders can be used dependent upon the procedure to be performed and the preference of the user.

While the handle shown and described herein is configured primarily to be held by the user with one hand while operating the controls with another, it will be appreciated that the handle can also have configurations which permit one handed operation of the needle holders including, but not limited to, configurations wherein the handle includes pivoted legs with finger loops, one fixed and one pivoted leg with finger loops, a pistol grip with one or more movable triggers, and/or resilient U-shaped members. Moreover, the handle can be formed with the housing as an integral one-piece unit and can have any orientation relative to the longitudinal axis of the instrument including, for example, substantially transverse orientations wherein the handle extends transversely relative to the longitudinal axis of the instrument, substantially longitudinal orientations wherein the handle is oriented substantially parallel to or at a small angle relative to the longitudinal axis of the instrument, or rotatable configurations wherein the handle can be moved between transverse and longitudinal orientations as desired.

The mechanisms shown for controlling operation of the needle holding members of the needle catcher and the needle driver and movement of the needle catcher and needle driver relative to one another are merely exemplary of the types of mechanisms that can be used to perform these functions. For example, in the case of slidable needle holding members, mechanisms including, but not limited to, controls in the form of push-buttons with wedge-shaped members for engaging flanges carried by each member, resilient U-shaped members with arms connected to each member, and triggers connected to the members via linkages or gears can be used to cause the needle holding members to move relative to one another. In the case of pivoted needle holding members or jaws, mechanisms such as tubular members movable relative to the jaws or linkages connecting one or both of the jaws with a trigger or the like at a proximal end of the instrument can be used to cause the needle holding member or jaws to move relative to one another. The needle holding members can be biased to a particular position, condition or state, such as an open state for receiving a suture needle or a closed state for grasping a suture needle, and can be provided with locking features to permit the user to maintain the members in a desired position.

Moving the needle driver and the needle catcher of the present invention relative to one another can be accomplished in any suitable manner, for example by connecting a knob at the proximal end of each needle holding instrument and sliding the knobs along slots formed in the handle housing or by mounting the needle holding instruments on geared components and moving the gears with a trigger or some other device. The particular length and curvature of the suture needles shown and described herein as well as any angular displacements of the needle driver and catcher shown and described herein are merely exemplary, and it will be appreciated that other needle lengths and angular displacements can be used. It will also be appreciated that the directions and angles of rotation of the needle driver and the needle catcher described and shown herein are for purposes of illustration only and can be reversed and/or altered in magnitude dependent upon procedural use and the preferences of the user.

While the needle driver and the needle catcher have been described herein as being independently controlled by separate operating mechanisms, such as push buttons slidably disposed along slots formed in the instrument housing, it will be appreciated that a single operating mechanism can be used to synchronize movement of the needle driver and the needle catcher relative to one another as well as operation of their respective needle holding members to further simplify the suturing process by allowing one-hand operation of the instrument. For example, a single operating mechanism utilizing conventional gearing and cam arrangements can enable the user to rotate the needle catcher toward a suture needle held by the needle driver in a first direction along an arcuate path in response to a single squeeze of a handle or trigger while also causing the jaws of the needle driver to open and the jaws of the needle catcher to close so that the suture needle is transferred or passed to the needle catcher. The user can then release the handle or trigger to cause the needle catcher to rotate away from the needle driver in a second, opposite direction along the arcuate path thereby pulling the suture needle through anatomical tissue. If desired, such an operating mechanism can move the needle driver toward the needle catcher when the handle is squeezed and also move the needle driver away from the needle catcher when the handle is released. Once the needle has been pulled through the tissue, the operating mechanism can reverse the process so that, for example, if the handle is squeezed again, the operating system will cause the needle catcher to rotate toward the needle driver in the first direction along the arcuate path while also causing the jaws of the needle catcher to open and the jaws of the needle driver to close, thereby transferring the suture needle back to the needle driver for continued suturing.

While the needle holders have been described herein as having a normally bent configuration which can be straightened by retracting the needle holders in a proximal direction relative to a tubular member so as to elastically deform the needle holders, it will be appreciated that the needle holders of the present invention can be moved between contracted and expanded positions using any suitable method including, but not limited to, methods utilizing linkages, gears, cables, movable stiffeners or inserts, shape memory materials, actuators or motors. Also, distal portions of the needle holders need not be straight as shown but can be curved or multiply angled, if desired.

The components of the suturing instrument of the present invention can be made of any suitable, medical grade materials to permit sterilization for reuse or disposal for single patient use. The components can be made of multiple parts of various configurations and materials to reduce cost. The handle and/or housing can have various valves, stop cocks and seals therein to control the flow of fluid and medical devices through the suturing instrument.

The features of the various embodiments described above can be combined in any manner desired dependent upon the operational requirements of the procedure to be performed and the complexity of the suturing instrument. It will also be appreciated that the suturing instrument of the present invention can be used to apply single or multiple stitches in open or endoscopic procedures.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An instrument for suturing anatomical tissue with a suture needle, said suturing instrument comprising
    an elongate tubular member having a proximal end and a distal end with a peripheral edge;
    a handle coupled to said proximal end;
    a driver arm extending from said distal end of said elongate tubular member and having a needle grasping portion, said driver arm being movable between an undeployed position where said needle grasping portion of said driver arm is disposed laterally inward of said peripheral edge of said elongate tubular member and a deployed position where said needle grasping portion of said driver arm is disposed laterally outward of said peripheral edge; and
    a catcher arm extending from said distal end of said elongate tubular member and having a needle grasping portion, said catcher arm being movable between an undeployed position where said needle grasping portion of said catcher arm is disposed laterally inward of said peripheral edge of said elongate tubular member and a deployed position where said needle grasping portion of said catcher arm is disposed laterally outward of said peripheral edge;
    at least one of said driver arm and said catcher arm being mounted for arcuate movement about a longitudinal axis of said elongate tubular member such that a corresponding needle grasping portion of said at least one of said driver arm and catcher arm is caused to move along an arcuate path having a radius of curvature greater than the distance between said longitudinal axis and said peripheral edge of said elongate tubular member;
    wherein said needle grasping portions are operable to grasp and release a suture needle so that, when said driver arm and said catcher arm are in said deployed positions, a suture needle having a radius of curvature commensurate with said radius of curvature of said arcuate path can be driven through the anatomical tissue using said driver arm and subsequently transferred to said catcher arm to be pulled through the anatomical tissue.

2. An instrument as recited in claim 1 wherein said needle holding portions of said driver arm and said catcher arm each include a pair of articulated needle holding members having needle holding surfaces radially spaced on opposite sides of said arcuate path when said driver arm and said catcher arm are in said respective deployed positions.

3. An instrument as recited in claim 2 wherein said needle holding members include a pair of pivotally opposed jaws.

4. An instrument as recited in claim 3 wherein both of said jaws move relative to one another.

5. An instrument as recited in claim 3 wherein a first of said jaws is fixed and a second of said jaws is movable relative to said first of said jaws.

6. An instrument as recited in claim 3 wherein said needle holding portion of said driver arm and said needle holding portion of said catcher arm each include inner and outer telescoping members axially movable relative to one another, said jaws being mounted at the distal end of said inner telescoping member and being biased apart to an open position such that relative axial movement of said inner and outer telescoping members results in opening and closing of said jaws.

7. An instrument as recited in claim 1 wherein each of said needle holding portion of said driver arm and said needle holding portion of said catcher arm includes a first needle holding member having a distal end in the form of a hook and a second needle holding member having a distal end movable relative to said hook to grasp and release suture needles disposed within said hook.

8. An instrument as recited in claim 1 wherein said driver arm and said catcher arm are longitudinally movable relative to said elongate tubular member between extended positions where said driver arm and said catcher arm bend outwardly in a lateral direction relative to a longitudinal axis of said elongate tubular member and retracted positions where said driver arm and said catcher arm are forced inwardly toward said longitudinal axis.

9. An instrument as recited in claim 8 wherein said driver arm and said catcher arm protrude distally from said distal end of said tubular member in said extended positions and are proximally spaced from said distal end of said tubular member in said retracted positions.

10. An instrument as recited in claim 1 wherein said driver arm and said catcher arm each include a straight proximal portion oriented substantially parallel to a longitudinal axis of said elongate tubular member and an angled distal portion extending laterally outward from said straight portion at an angle relative to said longitudinal axis when in a deployed position.

11. An instrument as recited in claim 10 wherein said driver arm and said catcher arm are axially movable relative to said elongate tubular member between a retracted position where said angled portion is moved laterally inward toward said undeployed position and an extended position where said angled portion is permitted to spread laterally outward toward said deployed position.

12. An instrument as recited in claim 1 and further comprising means for defining an operating channel through said elongate tubular member.

13. An instrument as recited in claim 12 wherein said means for defining includes an inner tubular member disposed within said elongate tubular member with a small radial clearance to define an annular space therebetween, at least one of said driver arm and said catcher arm being movably disposed within said annular space.

14. An instrument as recited in claim 12 wherein said means for defining extends through said elongate tubular member to define a longitudinal channel along the length of said instrument, and further comprising a coupling at a proximal end of said channel.

15. An instrument as recited in claim 12 wherein said means for defining extends through said elongate tubular member to define a longitudinal channel along the length of said instrument, and further comprising a valve disposed along said longitudinal channel to control passage of fluids and instruments therethrough.

16. An instrument as recited in claim 1 wherein said driver arm and said catcher arm are mounted for arcuate movement about said longitudinal axis of said elongate tubular member.

17. A method of suturing anatomical tissue using a length of suture material attached to a suture needle, said method comprising the steps of grasping the suture needle with a driver arm extending outwardly from a distal end of an elongate tubular member at an angle relative to a longitudinal axis of the elongate tubular member;

using the driver arm to drive the suture needle through the anatomical tissue in a first direction along an arcuate path having a radius of curvature substantially commensurate with the radius of curvature of the suture needle to cause the tip of the needle to penetrate the anatomical tissue;

receiving the tip of the suture needle in a catcher arm extending from the elongate tubular member;

grasping the suture needle with the catcher arm;

releasing the suture needle from the driver arm; and using the catcher arm to pull the suture needle through the anatomical tissue in the first direction along a second arcuate path having a radius of curvature substantially commensurate with the radius of curvature of the suture needle.

18. A method of suturing anatomical tissue as recited in claim 17 wherein said step of using the driver arm includes the step of rotating the elongate tubular member with the driver arm as a unit about the longitudinal axis of the elongate tubular member to drive the suture needle through the anatomical tissue.

19. A method of suturing anatomical tissue as recited in claim 18 wherein said step of receiving the suture needle in the catcher arm includes the steps of maintaining the driver arm in a substantially stationary position and rotating the catcher arm along an arcuate path about the longitudinal axis of the elongate tubular member in the direction of the driver arm.

20. A method of suturing anatomical tissue as recited in claim 17 and further comprising, prior to said step of using the driver arm, the step of causing a needle holding portion of the driver arm to move laterally outward from an undeployed position spaced inwardly of the peripheral edge of the elongate tubular member to a deployed position spaced outwardly of the peripheral edge of the elongate tubular member.

21. A method of suturing anatomical tissue as recited in claim 17 and further comprising, prior to said step of using the driver arm, the step of causing the driver arm to move distally relative to the elongate tubular member from a retracted position within the elongate tubular member to an extended position protruding from the distal end of the elongate tubular member.

22. A method of suturing anatomical tissue as recited in claim 17 and further comprising, after said step of releasing the suture needle from the driver arm, the steps of rotating the driver arm in a second direction opposite the first direction to receive the tip of the suture needle held by the catcher arm;

grasping the suture needle with the driver arm;

releasing the suture needle from the catcher arm; and rotating the driver arm in the first direction to cause the tip of the suture needle to penetrate through the anatomical tissue.

23. A method of suturing anatomical tissue using a length of suture material attached to a suture needle, said method comprising the steps of grasping the suture needle with a driver arm extending from a distal end of an elongate tubular member;

using the driver arm to drive the suture needle through the anatomical tissue in a first direction along an arcuate path having a radius of curvature substantially commensurate with the radius of curvature of the suture needle to cause the tip of the needle to penetrate the anatomical tissue;

receiving the tip of the suture needle in a catcher arm extending outwardly from the distal end of the elongate tubular member at an angle relative to a longitudinal axis of the elongate tubular member;

grasping the suture needle with the catcher arm;

releasing the suture needle from the driver arm; and using the catcher arm to pull the suture needle through the anatomical tissue in the first direction along a second arcuate path having a radius of curvature substantially commensurate with the radius of curvature of the suture needle.

24. A method of suturing anatomical tissue as recited in claim 23 wherein said step of using the driver arm includes the step of rotating the elongate tubular member with the driver arm as a unit about the longitudinal axis of the elongate tubular member to drive the suture needle through the anatomical tissue.

25. A method of suturing anatomical tissue as recited in claim 24 wherein said step of receiving the suture needle in the catcher arm includes the steps of maintaining the driver arm in a substantially stationary position and moving the catcher arm along an arcuate path in the direction of the driver arm.

26. A method of suturing anatomical tissue as recited in claim 23 and further comprising, prior to said step of using the catcher arm, the step of causing the catcher arm to move laterally outward from an undeployed position spaced inwardly of the peripheral edge of the elongate tubular member to a deployed position spaced outwardly of the peripheral edge of the elongate tubular member.

27. A method of suturing anatomical tissue as recited in claim 23 and further comprising, prior to said step of using the catcher arm, the step of causing the catcher arm to move distally relative to the elongate tubular member from a retracted position within the elongate tubular member to an extended position protruding from the distal end of the elongate tubular member.

28. A method of suturing anatomical tissue as recited in claim 23 and further comprising, after releasing the suture needle from the driver arm, the steps of rotating the driver arm in a second direction opposite the first direction to receive the tip of the suture needle held by the catcher arm;

grasping the suture needle with the driver arm;

releasing the suture needle from the catcher arm; and rotating the driver arm in the first direction to cause the tip of the suture needle to penetrate through the anatomical tissue.

29. A method of suturing anatomical tissue using a length of suture material attached to a suture needle, said method comprising the steps of grasping the suture needle with a driver arm extending outwardly from a distal end of an elongate tubular member at an angle relative to a longitudinal axis of the elongate tubular member;

using the driver arm to drive the suture needle through the anatomical tissue in a first direction along an arcuate path having a radius of curvature substantially commensurate with the radius of curvature of the suture needle to cause the tip of the needle to penetrate the anatomical tissue;

receiving the tip of the suture needle in a catcher arm extending outwardly from the distal end of the elongate tubular member at an angle relative to a longitudinal axis of the elongate tubular member;

grasping the suture needle with the catcher arm;

releasing the suture needle from the driver arm; and using the catcher arm to pull the suture needle through the anatomical tissue in the first direction along a second arcuate path having a radius of curvature substantially commensurate with the radius of curvature of the suture needle.

30. A method of suturing anatomical tissue as recited in claim 29 wherein said step of using the driver arm includes the step of rotating the elongate tubular member with the driver arm as a unit about the longitudinal axis of the elongate tubular member to drive the suture needle through the anatomical tissue.

31. A method of suturing anatomical tissue as recited in claim 30 wherein said step of receiving the suture needle in the catcher arm includes the steps of maintaining the driver arm in a substantially stationary position and moving the needle catcher along an arcuate path in the direction of the needle driver.

32. A method of suturing anatomical tissue as recited in claim 25 wherein, in said step of moving the catcher arm, the arcuate path has a radius of curvature centered on an axis extending through the elongate tubular member.

33. A method of suturing anatomical tissue as recited in claim 31 wherein, in said step of moving the catcher arm, the arcuate path has a radius of curvature centered on an axis extending through the elongate tubular member.

34. A method of suturing anatomical tissue as recited in claim 17 wherein said step of using the driver arm comprises rotating the driver arm in the first direction with respect to the elongate tubular member and said step of receiving the tip of the suture needle comprises moving the catcher arm a second direction toward the driver arm, said step of rotating and said step of moving being conducted simultaneously.

* * * * *